(12) United States Patent
Günzburg et al.

(10) Patent No.: US 7,022,319 B1
(45) Date of Patent: Apr. 4, 2006

(54) VECTORS CARRYING THERAPEUTIC GENES ENCODING ANTIMICROBIAL PEPTIDES FOR GENE THERAPY

(75) Inventors: Walter H. Günzburg, Mödling (AT); David Winder, Vienna (AT); Robert M. Saller, Munich (DE)

(73) Assignee: GSF - Forschungszentrum fuer Umwelt und Gesundheit GmbH, Neuherberg (DE)

( * ) Notice: Subject to any disclaimer, the term of this patent is extended or adjusted under 35 U.S.C. 154(b) by 0 days.

(21) Appl. No.: 08/999,690

(22) Filed: Sep. 8, 1997

Related U.S. Application Data

(63) Continuation of application No. PCT/EP96/01001, filed on Mar. 8, 1996.

(30) Foreign Application Priority Data

Mar. 9, 1995 (DK) .................................... 0243/95

(51) Int. Cl.
*A01N 65/00* (2006.01)
*A01N 63/00* (2006.01)
*A61K 48/00* (2006.01)
*C12N 15/74* (2006.01)
*C12N 15/00* (2006.01)

(52) U.S. Cl. ................. 424/93.1; 424/93.2; 424/93.21; 435/320.1; 435/325; 435/440; 435/455; 514/44

(58) Field of Classification Search ............ 435/320.1, 435/440, 455, 325; 514/44
See application file for complete search history.

(56) References Cited

U.S. PATENT DOCUMENTS

| | | | | |
|---|---|---|---|---|
| 4,822,608 A | | 4/1989 | Benton et al. .................. 424/98 |
| 5,124,263 A | * | 6/1992 | Temin et al. ............. 435/240.2 |
| 5,658,775 A | * | 8/1997 | Gilboa ..................... 435/172.3 |
| 5,863,904 A | | 1/1999 | Nabel et al. |
| 5,962,410 A | * | 10/1999 | Jaynes et al. .................. 514/12 |
| 6,022,735 A | * | 2/2000 | Curiel et al. ............. 435/320.1 |
| 6,027,722 A | * | 2/2000 | Hodgson ................. 424/93.21 |

FOREIGN PATENT DOCUMENTS

| | | |
|---|---|---|
| EP | 0415731 A2 | 3/1991 |
| WO | WO 89/11539 | 11/1989 |
| WO | WO 91/08753 | 6/1991 |
| WO | WO 93/07906 | 4/1993 |
| WO | WO 93/12251 | 6/1993 |
| WO | WO 94/29437 | 12/1994 |
| WO | WO 95/00178 | 1/1995 |
| WO | WO 95/01095 | 1/1995 |
| WO | WO 95/06415 | 3/1995 |
| WO | WO 95/13375 | 5/1995 |
| WO | WO 96/07748 | 3/1996 |
| WO | WO 96/28564 | 9/1996 |
| WO | WO 96/37623 | 11/1996 |
| WO | WO 97/01357 | 1/1997 |
| WO | WO 97/09440 | 3/1997 |
| WO | WO 99/20742 | 4/1999 |
| WO | WO 99/35280 | 7/1999 |

OTHER PUBLICATIONS

Verma et al. Gene Therapy- Promises, Problems and Prospects. Nature, vol. 389, pp. 239-242, Sep. 18, 1997.*
Orkin et al. Report and Recommendations of the Panel to Access the NIH Investment in Research on Gene Therapy. Distributed by the National Institutes of Health, Bethesda, MD or www.nih.gov, Dec. 7, 1995.*
Dougherty et al. A Promoterless Retroviral Vector Indicates that there are Sequences in U3 Required for 3'RNA Processing. PNAS, vol. 84, pp. 1197-1201, Mar. 1987.*
Perez-Paya et al. Biochem J 1994 Apr..;299:587-91.*
Perez-Paya et al. Pept Res 1994 7:286-8.*
Perez-Paya et al. J Biochem 1995 270:1048-56.*
Rivett et al. Biochem J 1996; 316:525-29.*
Peptides, Encyclopedia Britannica online, accessed Dec. 19, 2000.*
Günzburg, W. H., et al., "Retroviral Vectors Directed to Predefined Cell Types for Gene Therapy," *Biologicals*, 23: 5-12 (1995).

(Continued)

*Primary Examiner*—Q. Janice Li
(74) *Attorney, Agent, or Firm*—Jenkins, Wilson & Taylor, P.A.

(57) ABSTRACT

The present invention relates to recombinant vectors carrying sequences encoding naturally occurring antimicrobial peptides or derivatives thereof for the treatment of mammalian tumours and viral infections such as HIV infections and bacterial and fungal infections. In particular the present invention relates to retroviral vectors. Furthermore, the present invention relates to retroviral vectors which undergo promoter conversion (Procon vectors) carrying such sequences. Since these vectors also carry tumour or virus specific regulatory elements, the therapeutic antimicrobial peptide will be delivered and expressed only in relevant, affected cells and not in innocent bystander cells.

20 Claims, 20 Drawing Sheets

OTHER PUBLICATIONS

Boman, H. G., "Peptide Antibiotics and Their Role in Innate Immunity," *Annu. Rev. Immunol., 13*:61-92 (1995).

Moore, A.J., et al., "Preliminary Experimental Anticancer Activity of Cecropins," *Peptides Res., 7*(5):265-269 (1994).

Sharma, S.V., "Melittin-induced hyperactivation of phospholipase $A_2$ activity and calcium influx in ras-transformed cells," *Oncogene, 8*:939-947 (1993).

Sharma, S.V., "Melittin resistance: a counterselection for ras transformation," *Oncogene, 7*:193-201 (1992).

Ohsaki, Y., et al., "Antitumor Activity of Magainin Analogues Against Human Lung Cancer Cell Lines," *Cancer Res., 52*:3534-3538 (1992).

Wachinger, M. et al., "Influence of amphipathic peptides on the HIV-1 production in persistently infected T lymphoma cells," *FEBS, 309*(3):235-241 (1992).

Cruciani, R. A., et al., "Antibiotic magainins exert cytolytic activity against transformed cell lines through channel formatiom," *Proc. Natl. Acad. Sci. USA, 88*:3792-3796 (1991).

Lee, J. -Y., et al., "Antibacterial peptides from pig intestine: Isolation of a mammalian cecropin," *Proc. Natl. Acad. Sci. USA, 86*:9159-9162 (1989).

Vlasak, R., et al., "Nucleotide sequence of cloned cDNA coding for honeybee prepromelittin," *Eur. J. Biochem., 135*:123-126 (1983).

Hultmark, D., et al., "Insect Immunity: Isolation and Structure of Cecropin D and Four Minor Antibacterial Components from Cecropia Pupae," *Eur. J. Biochem., 127*: 207-217 (1982).

Steiner, H., et al., "Sequence and specificity of two antibacterial proteins involved in insect immunity," *nature, 292*:246-248 (1981).

Hultmark, D., et al., "Insect Immunity. Purification and Properties of Three Inducible Bactericidal Proteins from Hemolymph of Immunized Pupae of *Hyalophora cecropia,*" *Eur. J. Biochem., 106*:7-16 (1980).

Acha-Orbea et al., "Subversion of Host Immune Responses by Viral Superantigens", *Trends In Microbiology*, vol. 1 (No. 1); 32-34, Apr. 1993.

Knight et al., "Biochemical Analysis of the Mouse Mammary Tumor Virus Long Terminal Repaet Product. Evidence for the Molecular Structure of an Endogenous Superantigen", *European Journal of Immunology*, vol. 22; 879-882, 1992.

Salmons et al., "Production of Mouse Mammary Tumor Virus upon Transfection of a Recombinant Proviral DNA into Cultured Cells", *Virology*, vol. 144; 101-114, 1985.

Korman et al., "The Mouse Mammary Tumor Virus Long Terminal Repeat Encodes a Type II Transmembrane Glycoprotein", *The EMBO Journal*, vol. 11 (No. 5); 1901-1905, 1992.

Hornsby et al., "A Modified Procedure for Replica Plating of Mammalian Cells Allowing Selection of Clones Based on Gene Expression", *BioTechniques*, vol. 12 (No. 2); 244-251, 1992.

Günzburg et al., "Factors Controlling the Expression of Mouse Mammary Tumour Virus", *Biochemical Journal*, vol. 283; 625-632, 1992.

Huber, Brigitte T., "Mls Genes and Self-Superantigens", *TIG*, vol. 8 (No. 11); 399-402, Nov. 1992.

Salmons et al., "Current Perspectives in the Biology of Mouse Mammary Tumour Virus", *Virus Research*, vol. 8; 81-102, 1987.

Wintersperger, et al., "Negative-acting Factor and Superantigen Are Separable Activities of the Mouse Mammary Tumor Virus Long Terminal Repeat", *Proceedings of the National Academy of Sciences*; vol. 92; 2745-2749, Mar. 1995.

Donehower et al., "Regulatory and Coding Potential of the Mouse Mammary Tumor Virus Long Terminal Redundancy", *Journal of Virology*, vol. 37 (No.1): 226-238, Jan. 1981.

Vile et al., "In Vitro and In Vivo Targeting of Gene Expression to Melanoma Cells", *Cancer Research*, vol. 53 (No. 5); 962-967 (abstract only), 1993.

Choi et al., "A Superantigen Encoded in the Open Reading Frame of the 3' Long Terminal Repeat of Mouse Mammary Tomour Virus", *Nature*, vol. 350; 203-207, Mar. 1991.

Brandt-Carlson et al., "Detection and Characterization of a Glycoprotein Encoded by the Mouse Mammary Tumor Virus Long Terminal Repeat Gene", *Journal of Virology*, vol. 65 (No. 11); 6051-6060, Nov. 1991.

Acha-Orbea et al., "Clonal Deletion of V β14-bearing T Cells In Mice Transgenic for Mammary Tumour Virus", *Nature*, vol. 350; 207-211, Mar. 1991.

Brandt-Carlson et al., "Phylogenetic and Structural Analyses of MMTV LTR ORF Sequences of Exogenous and Endogenous Origins", *Virology*, vol. 193, 171-185, 1993.

Krummenacher et al., "The Mouse Mammary Tumor Virus Long Terminal Repeat Encodes A 47 kDa Glycoprotein With A Short Half-life In Mammalian Cells", *Molecular Immunology*, vol. 30 (No. 13); 1151-1157, 1993.

Winslow et al., "Detection and Biochemical Characterization of the Mouse Mammary Tumor Virus 7 Superantigen (Mls-1ᵃ)", *Cell*, vol. 71; 719-730, Nov. 1992.

Winslow et al., "Processing and Major Histocompatibility Complex Binding of the MTV7 Superantigen", *Immunity*, vol. 1; 23-33, Apr. 1994.

Kay et al., "In Vivo Gene Therapy of Hemophilia B: Sustained Partial Correction in Factor IX-deficient Dogs", *Science*, vol. 262 (No. 5130); 117-119, Oct. 1993.

Pullen et al., "The Open Reading Frames in the 3' Long Terminal Repeats of Several Mouse Mammary Tumor Virus Integrants Encode Vβ3-specific Superantigens", *Journal of Experimental Medicine*, vol. 175; 41-17, Jan. 1992.

Mohan et al., "Production and Characterization of an Mls-1-specific Monoclonal Antibody", *Journal of Experimental Medicine*, vol. 177; 351-358, Feb. 1993.

Genbank® Accession No. J02255.
Genbank® Accession No. M28246.
Genbank® Accession No. M28247.
Genbank® Accession No. M28248.

Definition of antisense DNA from *Stedman's Medical Dictionary*.

Scott et al., "Promoter-Proximal Poly (A) Sites Are Processed Efficiently, but the RNA Products Are Unstable in the Nucleus", *Molecular and Cellular Biology*, vol. 17 (No. 4); 2127-2135, Apr. 1997.

Faustinella et al., "A New Family of Murine Retroviral Vectors with Extended Multiple Cloning Sites for Gene Insertion", *Human Gene Therapy*, vol. 5; 307-312, 1994.

Mehigh et al., "Development of a Recombinant Bovine Leukemia Virus Vector for Delivery of a Synthetic Bovine Growth Hormone-Releasing Factor Gene into Bovine Cells", *Journal of Animal Science*, vol. 71; 687-693, 1993.

Mee et al., "Construction and Hormone Regulation of A Novel Retroviral Vector", *Gene*, vol. 88; 289-292, 1990.

dwPanganiban et al., "The Retrovirus pol Gene Encodes A Product Required for DNA Integration: Identification of A Retrovirus int locus", *Proceedings from the national Academy of Sciences*, vol. 81; 7885-7889, dec. 1984.

Longmore et al., "Both Megakaryocytopoiesis and Erythropoiesis Are Induced in Mice Infected With a Retrovirus Expressing an Oncogenic Erythropoietin Receptor", *Blood*, vol. 82 (No. 8); 2386-2395, Oct. 1993.

Panganiban et al., "The Terminal Nucleotides of Retrovirus DNA Are Required for Integration But Not Virus Production", *Nature*, vol. 306; 155-160, Nov. 1983.

Scarpa et al., "Characterization of Recombinant Helper Retroviruses from Moloney-Based Vectors in Ecotropic and Amphotropic Packaging Cell Lines", *Virology*, vol. 180; 849-852, 1991.

Felder et al., "Functional and Biological Properties of an Avian Variant Long Terminal Repeat Containing Multiple A to G Conversions in the U3 Sequence", *Journal of Virology*, vol. 68 (No. 8); 4759-4767, Aug. 1994.

Harper et al., "The p21 Cdk-Interacting Protein Cip 1 Is a Potent Inhibitor of G1 Cyclin-Dependent Kinases", *Cell*, vol. 75; 805-816, Nov. 1993.

Miller et al., "Improved Retroviral Vector for Gene Transfer and Expression", *Bio Techniques*, vol. 7 (No. 9); 980-990, 1989.

Price et al., "Lineage Analysis in The Vertebrate Nervous System by Retrovirus-mediated Gene Transfer", *Proceedings from the National Academy of Sciences*, vol. 84; 156-160, Jan. 1987.

Feldman et al., "Prevention of Restenosis After Coronary Angioplasty: Towards a Molecular Approach", *Fundamental & Clinical Pharmacology*, vol. 9; 8-16, 1995.

Crystal, Ronald F., "Transfer of Genes to Humans: Early Lessons and Obstacles to Success", *Science*, vol. 270; 404-410, 1995.

Tsang et al., "Induction of Human Cytotoxic T Cell Lines Directed Against Point-Mutated p21 Ras-Derived Synthetic Peptides", *Vaccine Research*, vol. 3 (No. 4); 183-193, 1994.

Härtig et al., "Regulation of Expression of Mouse Mammary Tumor Virus Through Sequences Located in the Hormone Response Element: Involvement of Cell-Cell Contact and a Negative Regulatory Factor", *Journal of Virology*, vol. 67 (No. 2); 813-821, Feb. 1993.

Nakanishi et al., "Identification of the Active Region of the DNA Synthesis Inhibitory Gene $p21^{Sdi1,CIP1/WAF1}$" *The EMBO Journal*, vol. 14 (No. 3); 555-563, 1995.

Noda et al., "Cloning of Senescent Cell-Derived Inhibitors of DNA Synthesis Using an Expression Screen", *Experimental Cell Research*, vol. 211; 90-98, 1994.

Stange et al., "Prolonged Biochemical and Morphological Stability of Encapsulated Liver Cells—A New Method", *Biomaterials, Artificial Cells and Immobilization Biotechnology*, vol. 21 (No. 3); 343-352, 1993.

Katayose et al., "Consequences of p53 Gene Expression By Adenovirus Vector On Cell Cycle Arrest and Apoptosis In Human Aortic Vascular Smooth Muscle Cells", *Biochemical And Biophysical Research Communications*, vol. 215 (No. 2); 446-451, Oct. 1995.

Bond et al., "Mutant p53 Rescues Human Diploid Cells from Senescence Without Inhibiting the Induction of SDl1/WAF1", *Cancer Research*, vol. 55; 2404-2409, Jun. 1995.

Skotzko et al., "Retroviral Vector-mediated Gene Transfer of Antisense Cyclin G1 (CYCG1) Inhibits Proliferation of Human Osteogenic Sarcoma Cells", *Cancer Research*, vol. 55; 5493-5498, Dec. 1995.

Nakanishi et al., "Exit From $G_0$ and Entry Into the Cell Cycle of Cells Expressing $p21^{Sdi1}$ Antisense RNA", *Proceedings from the national Academy of Sciencees*, vol. 92; 4352-4356, May 1995.

Zakut et al., "The Tumor Suppression Function of $p21^{Waf}$ ('half-WAF')", *Oncogene*, vol. 11; 393-395, 1995.

Johnson et al., "Evidence for a p53-Independent Pathway for Upregulation of SDl1/CIP1/WAF1/p21 RNA in Human Cells", *Molecular Carcinogenesis*, vol. 11; 59-64, 1994.

Rubelj et al., "SV40-Transformed Human Cells in Crisis Exhibit Changes That Occur in Normal Cellular Senescence", *Experimental Cell Research*, vol. 211; 82-89, 1994.

Xiong et al., "p21 Is a Universal Inhibitor of Cyclin Kinases", *Nature*, vol. 366; 701-704, Dec. 1993.

Günzburg et al., "A Mammary-Specific Promoter Directs Expression of Growth Hormone not only to the Mammary Gland, but also to Bergman Glia Cells in Transgneic Mice", *Molecular Endocrinology*, vol. 5 (No. 1); 123-133, 1991.

Hunter, Tony, "Braking the Cycle", *Cell*, vol. 75, 839-841, Dec. 1993.

El-Deiry et al., "WAF1, a Potential Mediator of p53 Tumor Suppression", *Cell*, vol. 75; 817-825, Nov. 1993.

Junker et al., "Genetic Instability of a MoMLV-based Antisense Double-copy Retroviral Vector Designed for HIV-1 Gene Therapy", *Gene Therapy*, vol. 2; 639-646, 1995.

Günzburg et al., "Retroviral Vectors Directed to Predefined Cell Types for Gene Therapy", *Biologicals*, vol. 23; 5-12, 1995.

Couture et al., "Retroviral Vectors Containing Chimeric Promoter/Enhancer Elements Exhibit Cell-Type-Specific Gene Expression", *Human Gene Therapy*, vol 5; 667-677, 1994.

Salmons et al., "Targeting of Retroviral Vectors for Gene Therapy", *Human Gene Therapy*, vol. 4; 129-141, 1993.

Cannon et al., "Murine Leukemia Virus-Based Tat-Inducible Long Terminal Repeat Replacement Vectors: a New System for Anti-Human Immunodeficiency Virus Gene Therapy", *Journal of Virology*, vol. 70 (No. 11); 8234-8240, Nov. 1996.

Robinson et al., "Retroviral Vector With a CMV-IE/HIV-TAR Hybrid LTR Gives High Basal Expression Levels and Is UP-Regulated by HIV-1 Tat", *Gene Therapy*, vol. 2; 269-278, 1995.

Ferrari et al., "A Retroviral Vector Containing a Muscle-Specific EnHancer Drives Gene Expression Only in Differentiated Muscle Fibers", *Human Gene Therapy*, vol. 6; 733-742, Jun. 1995.

Vile et al., "Tissue-Specific Gene Expression from Mo-MLV Retroviral Vectors with Hybrid LTRs Containing the Murine Tyrosinase Enhancer/Promoter", *Virology*, vol. 214; 307-313, 1995.

Günxburg et al., "Endogenous Superantigen Expression Controlled by a Novel Promoter in the MMTV Long Terminal Repeat", *Nature*, vol. 364; 154-158, Jul. 1993.

Salmons et al., "naf, a trans-Regulating Negative-Acting Factor Encoded Within the Mouse Mammary Tumor Virus Open Reading Frame Region", *Journal of Virology*, vol. 64 (No. 12); 6355-6359, Dec. 1990.

Definition of "Provirus" from *Dorland's Illustrated Medical Dictionary*, 28th Edition, W.B. Saunders Co., 1373, 1994.

Fasel et al., "The Region of Mouse Mammary Tumor Virus DNA Containing the Long Terminal Repeat Includes a Long Coding Sequence and Signals for Hormonally Regulated Transcription", *The EMBO Journal*, vol. (No. 1); 3-7, 1982.

Wintersperger et al., "A Transient Assay for Gene Expression Studies in B Lymphocytes and It's use for Superantigen Assays", *BioTechniques*, vol. 16 (No. 5), 882-886, 1994.

Genbank® Accession No. V01175.

Wintersperger et al., "Superantigen and NAF Activities of Mouse Mammary Tumour Virus Can Be Separated", *Journal of Cellular Biochemistry*, Supplemental 17D:54, Mar. 1993.

Jane et al., "Vector Development: A Major Obstacle in Human Gene Therapy", *Annals of Medicine*, vol. 30 (No. 5); 413-415, Oct. 1998.

Kaplitt et al., "Genetic Modification of Cells with Retrovirus Vectors", *Viral Vectors*, M.G. Kaplitt et al., eds. (San Diego, CA: Academic Press, Inc.); 215-216 and 299, 1995.

Guntaka, Ramareddy V., "Transcription Termination and Polyadenylation in Retroviruses", *Microbiological Reviews*, vol. 57 (No. 3); 511-521, Sep. 1993.

Couto, M.A., et al., "Inhibition of Intracellular *Histoplama capsulatum* Replication by Murine Macrophages That Produce Human Defensin," *Infection and Immunity, 62(6)*: 2375-2378 (Jun., 1994).

* cited by examiner

VECTORS CARRYING THERAPEUTIC GENES ENCODING ANTIMICROBIAL PEPTIDES FOR GENE THERAPY

RELATED APPLICATIONS

This is a continuation application of PCT/EP96/01001 filed Mar. 8, 1996, which claims priority to Danish patent application DK 0243/95 filed Mar. 9, 1995. The contents of PCT/EP96/01001 and DK 0243/95 are incorporated herein by reference in their entirety.

BACKGROUND OF THE INVENTION

The introduction of therapeutic genes into cells for the treatment of diseases as diverse as those resulting from genetic defects, cancer and viral infections is the major aim of gene therapy. Cancer and diseases such as AIDS resulting from infection with human immunodeficiency virus (HIV) are particularly difficult to treat even though a number of clinical protocols are presently underway that use gene therapeutical approaches. The amphipathic peptide melittin, the major component of bee venom, has been shown to have selective anti-cancer (Sharma, S. V., *Oncogene*, 7:193–201 (1992); Sharma, S. V., *Oncogene*, 8:939–947 (1993)) and anti-HIV activity (Wachinger et al., *FEBS Lett.*, 309:235–241 (1992)); U.S. Pat. No. 4,822,608 of Benton et al. and WO patent application 91/08753 of Erfle et al. both relate to these therapeutic properties.

U.S. Pat. No. 4,822,608 issued to Benton et al. on Apr. 18, 1989 and entitled "METHODS AND COMPOSITIONS FOR THE TREATMENT OF MAMMALIAN INFECTIONS EMPLOYING MEDICAMENTS COMPRISING HYMENOPTERA VENOM OR PROTEINACEOUS OR POLYPEPTIDE COMPONENTS THEREOF" teaches that secondary agents derived from nature such as *hymenoptera* venom or proteinaceous or polypeptide components thereof has a potentiating effect on antibacterial agents. This reference further suggests that such compositions may also have increased anti-viral, carcinostatic and anti-carcinogenic effects on various maladies. More particularly, the reference to Benton et al. discloses the use of melittin which is the main component of honey bee toxin, in combination with assorted antibiotic agent as having antibacterial activity against predetermined infections. Further this reference teaches that a synergistic benefit may be achieved by the combination of the melittin and assorted antibiotics in various therapeutically effective amounts.

WO patent application 91/08753 of Erfle et al. relates to a method and composition for the treatment of mammalian HIV infections, and more particularly to such a method and composition for treating mammalian HIV infections which employs *hymenoptera* venom, or proteinaceous or polypeptide components thereof and which is introduced into the mammalian hosts and which are individually operable to restrict or substantially inhibit the virus replication in the HIV infected cells of the mammal.

In these studies purified melittin peptide was given to cells in culture which, though useful for experimental purposes, is not relevant for therapy. Even in vivo administration of purified melittin protein (for example i.v.) is probably not advisable because of the relatively high concentrations and repeated doses that would be required to maintain therapeutic levels. Further, since this kind of generalized delivery would result in the amphipathic peptide reaching not only target cells but also other cells, thereby potentially resulting in nondesirable side effects, it would be advantageous to be able to target the delivery of melittin or other antimicrobial peptides, in particular the melittin peptide and the peptides mentioned below.

A second class of therapeutic genes of interest are the cecropins isolated from the pupae of giant silk moths (Bowman, H. G., *Ann. Rev. Immunol.*, 13:1–51 (1995), Hultmark et al., *Eur. J. Biochem.*, 106:7–16 (1980)). There are three principal cecropins, A, B and D with a similar structure to melittin (Hultmark et al., *Eur. J. Biochem.*, 127:207–217 (1982)). Cecropins A and B show specific antibacterial activity without any apparent ill effects for mammalian cells (Steiner H. et al., *Nature*, 292:246–248 (1991)). Recently Moore and coworkers have shown that the cecropin B, P and Shiva-1 antibacterial peptides show anticancer activity against a variety of tumour cell lines (Moore, A. J. et al., *Peptide Research*, 7:265–269 (1994)).

Cecropins were first isolated from the hemolymph of the giant silk moth, *Hyalophora cecropia*, following induction by live non-pathogenic bacteria. The principal insect cecropins (A, B and D) are 35 to 37 residues long, devoid of cystein and have a strongly basic N-terminus linked to a neutral C-terminius by a flexible glycine-proline link. The overall structure deduced by NMR for cecropin A is two nearly perfect amphipathic segments joined by a Gly-Pro hing. A cecropin-like 31-residue peptide (cecropin P), isolated from the small intestine of a pig (Lee et al., Proc. Natl. Acad. Sci. USA, 86:9159–9162 (1989)), suggests that the cecropins may be widespread throughout the animal kingdom. The mechanism of action of the cecropins is thought to involve channel formation in membranes and subsequent lysis.

SB-37 (a close cecropin B analogue) and Shiva-1 (a cecropin B analogue that shares about 40% sequence homology and maintains the same charge distribution and hydrophobicity as the peptide) have been shown to lyse several mammalian leukemia and lymphoma cell lines in vitro. The publication of Moore, A. J. et al., *Peptide Research*, 7:265–269 (1994) is incorporated herein by reference for complete disclosure. Similar antitumour effects have been demonstrated for the magainins, a related group of antimicrobial peptides (Cruciani, R. A. et al., *Proc. Natl. Acad. Sci. USA*, 88:3792–3796 (1991); Ohaski, Y. et al., *Cancer Research*, 52:3534–3538, (1992)).

The use of retroviral vectors (RV) for gene therapy has received much attention and currently is the method of choice for the transferral of therapeutic genes in a variety of approved protocols both in the USA and in Europe (Kotani, H. et al., *Human Gene Therapy*, 5:19–28 (1994)). However most of these protocols require that the infection of target cells with the RV carrying the therapeutic gene occurs in vitro, and successfully infected cells are then returned to the affected individual (Rosenberg, S. A. et al., *Human Gene Therapy*, 3:75–90 (1992); for a review see Anderson, W. F., *Science*, 256:808–813 (1992)). Such ex vivo gene therapy protocols are ideal for correction of medical conditions in which the target cell population can be easily isolated (e.g. lymphocytes). Additionally the ex vivo infection of target cells allows the administration of large quantities of concentrated virus which can be rigorously safety tested before use.

Unfortunately, only a fraction of the possible applications for gene therapy involve target cells that can be easily isolated, cultured and then reintroduced. Additionally, the complex technology and associated high costs of ex vivo gene therapy effectively preclude its disseminated use world-wide. Future facile and cost-effective gene therapy will require an in vivo approach in which the viral vector, or cells producing the viral vector, are directly administered to the patient in the form of an injection or simple implantation of RV producing cells.

This kind of in vivo approach, of course, introduces a variety of new problems. First of all, and above all, safety considerations have to be addressed. Virus will be produced, possibly from an implantation of virus producing cells, and there will be no opportunity to precheck the produced virus. It is important to be aware of the finite risk involved in the use of such systems, as well as trying to produce new systems that minimize this risk.

The essentially random integration of the proviral form of the retroviral genome into the genome of the infected cell led to the identification of a number of cellular proto-oncogenes by virtue of their insertional activation (Varmus, H., *Science*, 240:1427–1435 (1988)). The possibility that a similar mechanism may cause cancers in patients treated with RVs carrying therapeutic genes intended to treat other pre-existent medical conditions, has posed a recurring ethical problem. Most researchers would agree that the probability of a replication defective RV, such as all those currently used, integrating into or near a cellular gene involved in controlling cell proliferation is vanishingly small. However, it is generally also assumed that the explosive expansion of a population of replication competent retrovirus from a single infection event, will eventually provide enough integration events to make such a phenotypic integration a very real possibility.

Retroviral vector systems are optimized to minimize the chance of replication competent virus being present. However, it has been well documented that recombination events between components of the RV system can lead to the generation of potentially pathogenic replication competent virus and a number of generations of vector systems have been constructed to minimize this risk of recombination (reviewed in Salmons, B. and Günzburg, W. H., *Human Gene Therapy*, 4:129–141 (1993)). However little is known about the finite probability of these events. Since it will never be possible to reduce the risk associated with this or other viral vector systems to zero, an informed risk-benefit decision will always have to be taken. Thus it becomes very important to empirically determine the chance of (1) insertional disruption or activation of single genes by retrovirus integration and (2) the risk of generation of replication competent virus by recombination in current generations of packaging cell lines. A detailed examination of the mechanism by which these events occur will also allow the construction of new types of systems designed to limit these events.

A further consideration for practical in vivo gene therapy, both from safety considerations as well as from an efficiency and from a purely practical point of view, is the targeting of RVs. It is clear that therapeutic genes carried by vectors should not be indiscriminately expressed in all tissues and cells, but rather only in the requisite target cell. This is especially important if the genes to be transferred are toxin genes aimed at ablating specific tumour cells. Ablation of other, nontarget cells would obviously be very undesirable. Targeting of the expression of carried therapeutic genes can be achieved by a variety of means.

Retroviral vector systems consist of two components (FIG. 1):
1) the retroviral vector itself is a modified retrovirus (vector plasmid) in which the genes encoding for the viral proteins have been replaced by therapeutic genes optionally including marker genes to be transferred to the target cell. Since the replacement of the genes encoding for the viral proteins effectively cripples the virus it must be rescued by the second component in the system which provides the missing viral proteins to the modified retrovirus.

The second component is:
2) a cell line that produces large quantities of the viral proteins, however lacks the ability to produce replication competent virus. This cell line is known as the packaging cell line and consists of a cell line transfected with a second plasmid carrying the genes enabling the modified retroviral vector to be packaged. This plasmid directs the synthesis of the necessary viral proteins required for virion production.

To generate the packaged vector, the vector plasmid is transfected into the packaging cell line. Under these conditions the modified retroviral genome including the inserted therapeutic and optional marker genes is transcribed from the vector plasmid and packaged into the modified retroviral particles (recombinant viral particles). A cell infected with such a recombinant viral particle cannot produce new vector virus since no viral proteins are present in these cells. However the vector carrying the therapeutic and marker genes is present and these can now be expressed in the infected cell.

SUMMARY OF THE INVENTION

It is an object of the present invention to provide a novel therapeutic agent with antitumour, antiviral, antibacterial and/or antifungal activities.

It is a further object of the present invention to provide a novel therapeutic agent with high selectivity for selected target cells and reduced nondesirable side effects.

To achieve the foregoing and other objects, the present invention provides a recombinant vector for introducing into an eucaryotic cell DNA, the vector comprising, in operable linkage, a) the DNA of or corresponding to at least a portion of a vector, which portion is capable of infecting and directing the expression in the target cells; and b) one or more coding sequences wherein at least one sequence encodes for at least one naturally occurring therapeutic antimicrobial peptide or a derivative thereof for the treatment of at least one disease, selected from mammalian tumours, viral, bacterial and fungal infections. Said sequence is preferably replication-defective.

Said sequence encoding a naturally occurring therapeutic antimicrobial peptide or derivative thereof encodes for the amino acid sequences of all, part, an analogue, homologue, recombinant or combination thereof of such antimicrobial peptide.

Said sequences comprise preferably also non-coding sequences.

The antimicrobial peptides or derivatives thereof include but are not limited to those encoding melittin, the various cecropins and magainins. Further included are the apidaecin and defensin peptides or derivatives thereof. These genes may be expressed in their preproform or alternatively in a genetically engineered preform or in another form which renders a biological active peptide or a derivative thereof.

Said sequence is preferably a recombinant molecule coding for the amino acid sequences of all, part, and analogue, homologue, derivative, recombinant or combination thereof of the melittin, cecropin, magainin, apidaecin and defensin genes.

As discussed in detail in the prior art reference to Benton et al., melittin, the main component in honey bee toxin is a polypeptide which includes substantially 26 amino acid residues. These amino acid residues include, Gly-Ile-Gly-Ala-Val-Leu-Lys-Val-Leu-Thr-Thr-Gly-Leu-Pro-Ala-Leu-Ile-Ser-Trp-Ile-Lys-Arg-Lys-Arg-Gln-Gln (SEQ ID NO: 1). Moreover, melittin analogues wherein at least the last six (C-terminal) amino acids is altered and replaced by six glycine residues appear to have a therapeutic benefit similar to melittin, these amino acid analogues having a structure of Gly-Ile-Gly-Ala-Val-Leu-Lys-Val-Leu-Thr-Thr-Gly-Leu-Pro-Ala-Leu-Ile-Ser-Trp-Ile-Gly-Gly-Gly-Gly-Gly-Gly (SEQ ID NO: 2). The use of melittin for treatment of HIV infections is disclosed in WO patent application 91/08753 of Erfle et al., which is incorporated herein by reference for complete disclosure. According to a preferred embodiment of the invention said structural analogue of melittin is Gly-Iie-Gly-Ala-Val-Leu-Lys-Val-Leu-Thr-Thr-Gly-Leu-Pro-Ala-Leu-Ile-Ser-Trp-Ile-Gly-Gly-Gly-Gly-Gly-Gly (SEQ ID NO: 2) or, according to a further preferred embodiment, Amfi 1 or 2 and peptides of GP 41 that are melittin-like.

According to a further preferred embodiment of the invention, the sequence encoding a therapeutic antimicrobial peptide is coding for a *hymenoptera* venom, at least one active protein component of a *hymenoptera* venom, at least one polypeptide component of a *hymenoptera* venom, and mixtures thereof.

The *hymenoptera* gene is preferably selected from the group consisting of genes coding for honey bee venom, bumble bee venom, yellow jacket venom, bald-faced hornet venom, active protein components of said venom, active protein components of said venom, and mixtures thereof.

Furthermore, the structural analogues of melittin include an amphophilic helix with or without signal peptide and activation domains.

In a preferred embodiment, the recombinant vector is selected from viral and plasmid vectors. Examples for viral vectors are RNA and DNA virus vectors. A particularly preferred RNA virus vector is a retrovirus vector, more particularly a procon vector. Examples for DNA virus vectors are adenoviruses, adenovirus associated viruses and herpes viruses derived vectors. The plasmid vectors include all eurcaryotic expression vectors.

In a preferred embodiment of the invention, the recombinant vector is a retroviral vector.

The retroviral genome consists of an RNA molecule with the structure R-U5-gag-pol-env-U3-R (FIG. 1). During the process of reverse transcription, the U5 region is duplicated and placed at the right hand end of the generated DNA molecule, whilst the U3 region is duplicated and placed at the left hand end of the generated DNA molecule (FIG. 1). The resulting structure U3-R-U5 is called LTR (Long Terminal Repeat) and is thus identical and repeated at both ends of the DNA structure or provirus. The U3 region at the left hand end of the provirus harbours the promoter. This promoter drives the synthesis of an RNA transcript initiating at the boundary between the left hand U3 and R regions and terminating at the boundary between the right hand R and U5 region (FIG. 1). This RNA is packaged into retroviral particles and transported into the target cell to be infected. In the target cell the RNA genome is again reverse transcribed as described above.

According to another embodiment of the invention a promoter conversion vector (procon vector) can be constructed in which the righthand U3 region is altered (FIG. 3), but the normal lefthand U3 structure is maintained (FIG. 3); the vector can be normally transcribed into RNA utilizing the normal retroviral promoter located within the left hand U3 region (FIG. 3). However the generated RNA will only contain the altered righthand U3 structure. In the infected target cell, after reverse transcription, this altered U3 structure will be placed at both ends of the retroviral structure (FIG. 3).

If the altered region carries a polylinker instead of the U3 region then any promoter, including those directing tissue specific expression such as the WAP promoter can be easily inserted. This promoter will then be utilized exclusively in the target cell for expression of linked genes carried by the retroviral vector. Alternatively or additionally DNA segments homologous to one or more cellular sequences can be inserted into the polylinker for the purpose of gene targeting.

In the packaging cell line the expression of the retroviral vector is thus regulated by the normal unselective retroviral promoter (FIG. 3). However as soon as the vector enters the target cell promoter conversion occurs, and the therapeutic genes are expressed from a tissue specific promoter of choice introduced into the polylinker (FIG. 3). Not only can virtually any tissue specific promoter be included in the system, providing for the selective targeting of a wide variety of different cell types, but additionally, following the conversion event, the structure and properties of the retroviral vector no longer resembles that of a virus. This, of course, has extremely important consequences from a safety point of view, since ordinary or state of the art retroviral vectors readily undergo genetic recombination with the packaging vector to produce potentially pathogenic viruses. Promoter conversion (Procon) vectors do not resemble retroviruses because they no longer carry U3 retroviral promoters after conversion thus reducing the possibility of genetic recombination inserted into the polylinker for the purposes of gene targeting.

For a complete disclosure of the procon vectors, the content of the Danish application DK 1017/94, filed on Sep. 2, 1994 is completely included within the present application or incorporated herein by reference.

Thus in a further preferred embodiment of the invention a retroviral vector undergoing promoter conversion (procon vector) is provided comprising a 5'LTR region of the structure U3-R-U5; one or more coding sequences wherein at least one of said coding sequences encodes a naturally occurring antimicrobial peptide or a derivative thereof (part, an analogue, homologue, recombinants or a combination thereof of such antimicrobial gene) for the treatment of at least one disease selected from mammalian tumours, viral infections, bacterial infections and fungal infections; and a 3'LTR region comprising a completely or partially deleted U3 region wherein said deleted U3 region is replaced by a polylinker sequence, followed by the R and U5 region.

And in a further preferred embodiment a retroviral vector is provided wherein said retrovirus vector includes, in operable linkage, a 5'LTR region and a 3'LTR region, said 5'LTR region comprising the structure U3-R-U5 and said 3'LTR region comprising a completely or partially deleted U3 region wherein said deleted U3 region is replaced by one or more of said coding sequences wherein at least one sequence encodes for at least one naturally occurring therapeutic antimicrobial peptide or a derivative thereof for the treatment of at least one disease, selected from mammalian tumours, viral, bacterial and fungal infections expressed from either the viral or a heterologous promoter, followed by the R and U5 region.

According to the invention the term "polylinker" is used for a short stretch of artificially synthesized DNA which carries a number of unique restriction sites allowing the easy insertion of any promoter or DNA segment. The term "heterologous" is used for any combination of DNA sequences that is not normally found intimately associated in nature. According to the invention, the heterologous DNA fragment can encode for example a peptide such as a marker peptide (e.g., β-galactosidase, neomycin, alcohol dehydrogenase, puromycin, hypoxanthine phosphoribosyl transferase (HPRT), hygromicin, and secreted alkaline phosphatase), a therapeutic peptide (e.g., herpes simplex virus thymidine kinase, cytosine deaminase, guanine phosphoribosyl transferase (gpt), and cytochrome P 450), a cell cycle regulatory peptide (e.g., P.T.O., SDI), a tumor suppressor peptide (e.g., p53), an antiproliferation peptide and a cytokine (e.g., IL-2).

With reference to the procon vectors, said polylinker sequence carries at least one unique restriction site and contains preferably at least one insertion of a heterologous DNA fragment. Said heterologous DNA fragment is preferably selected from regulatory elements and promoters, preferably being target cell specific in their expression. The retroviral promoter structure is termed LTR. LTR's carry signals that allow them to jump in and out of the genome of the target cell. Such jumping transposable elements can also contribute to pathogenic changes. Procon vectors can carry modified LTR's that no longer carry the signals required for jumping. Again this increases the potential safety of these vector systems.

Gene expression is regulated by promoters. In the absence of promoter function a gene will not be expressed. The normal MLV retroviral promoter is fairly unselective in that it is active in most cell types. However a number of promoters exist that show activity only in very specific cell types. Such tissue-specific promoters will be the ideal candidates for the regulation of gene expression in retroviral vectors, limiting expression of the therapeutic genes to specific target cells.

The target cell specific regulatory elements and promoters are preferably, but not limited to one or more elements of the group consisting of, Whey Acidic Protein (WAP), Mouse Mammary Tumour Virus (MMTV), β-lactoglobulin and casein specific regulatory elements and promoters, which may be used to target human mammary tumours, pancreas specific regulatory elements and promoters including carbonic anhydrase II and β-glucokinase regulatory elements and promoters, lymphocyte specific regulatory elements and promoters including human immunodeficiency virus (HIV), immunoglobulin and MMTV lymphocytic specific regulatory elements and promoters and MMTV specific regulatory elements and promoters such as $^{MMTV}$P2 conferring responsiveness to glucocorticoid hormones or directing expression to the mammary gland, T-cell specific-regulatory elements and promoters such as T-cell receptor gene and CD4 receptor promoter and B-cell specific regulatory elements and promoters such as immunoglobulin promoter or mb1. Said regulatory elements and promoters regulate preferably the expression of at least one of the coding sequences of said retroviral vector.

The LTR regions are preferably, but not limited, selected from at least one element of the group consisting of LTR's of Murine Leukaemia Virus (MLV), Mouse Mammary Tumour Virus (MMTV), Murine Sarcoma Virus (MSV), Simian. Immunodeficiency Virus (SIV), Human Immunodeficiency Virus (HIV), Human T-cell Leukaemia Virus (HTLV), Feline Immunodeficiency Virus (FIV), Feline Leukaemia Virus (FELV), Bovine Leukaemia Virus (BLV), and Mason-Pfizer-Monkey Virus (MPMV).

The antimicrobial genes of the present invention will be placed under the transcriptional control of for instance the HIV promoter or a minimal promoter placed under the regulation of the HIV tat responsive element (TAR) to target HIV infected cells. Targeting will be achieved because the HIV promoter is dependent upon the presence of Tat, and HIV encoded autoregulatory protein (Haseltine, W. A., *FASEB J.*, 5:2349–2360 (1991)). Thus only cells infected with HIV and therefore expressing Tat will be able to produce the amphipathic peptide introduced in the Procon vector (FIG. 2). Alternatively, the amphipathic peptide could be expressed from T cell specific promoters such as that from the CD4 or T cell receptor gene. In order to target tumour cells, promoters from genes known to be overexpressed in these cells (for example c-myc, c-fos) may be used.

The antimicrobial genes of the present invention may be placed also under the transcriptional control of other promoters known in the art. Examples for such promoters are of the group of SV40, cytomegalovirus, Rous sarcoma virus, β-actin, HIV-LTR, MMTV-LTR, B or T cell specific promoters, tumour specific promoters and HIV.

The retroviral vector is in one embodiment of the invention a BAG vector (Price, J. et al., *Proc. Natl. Acad. Sci. USA*, 87:156–160 (1987)), but includes also other retroviral vectors.

According to a preferred embodiment of the invention at least one retroviral sequence encoding for a retroviral protein involved in integration of retroviruses is altered or at least partially deleted. Said heterologous DNA fragment is preferably homologous to one or more cellular sequences. The regulatory elements and promoters are preferably regulatable by transacting molecules.

In a further embodiment of the invention a retroviral vector system is provided comprising a retroviral vector as described above as a first component and a packaging cell line harbouring at least one retroviral or recombinant retroviral construct coding for proteins required for said retroviral vector to be packaged.

The packaging cell line harbours retroviral or recombinant retroviral constructs coding for those retroviral proteins which are not encoded in said retroviral vector. The packaging cell line is preferably selected from an element of the group consisting of ψ2, ψ-Crip, ψ-AM, GP+E-86, PA317 and GP+envAM-12.

After replicating the retroviral vector of the invention as described above in a retroviral vector system as described above, a retroviral provirus is provided wherein said polylinker and any sequences inserted in said polylinker in the 3'LTR become duplicated during the process of reverse transcription in the infected target cell and appear in the 5'LTR as well as in the 3'LTR of the resulting provirus.

The retroviral vector of the invention refers to a DNA sequence retroviral vector on the DNA sequence level.

The invention includes, however, also a retroviral provirus and mRNA of a retroviral provirus according to the invention and any RNA resulting from a retroviral vector according to the invention and cDNAs thereof.

A further embodiment of the invention provides non-therapeutical or therapeutical method for introducing homologous and/or heterologous nucleotide sequences into human or animal cells in vitro and in vivo comprising transfecting a packaging cell line of a retroviral vector system according to the invention with a retroviral vector according to the invention and infecting a target cell population with recombinant retroviruses produced by the packaging cell line. The nucleotide sequences are selected from one or more elements of the group consisting of genes or parts of genes encoding for therapeutic antimicrobial peptides, regulatory sequences and promoters.

The retroviral vector, the retroviral vector system and the retroviral provirus as well as RNA thereof is used for producing a pharmaceutical composition for somatic gene therapy in mammals including humans. Furthermore, they are used for targeted integration in homologous cellular sequences.

Principle for the Construction of Procon Vectors for Targeted Gene Expression

In the Murine Leukemia Virus (MLV) retroviral vector known as BAG (Price, J. et al., *Proc. Natl. Acad. Sci. USA*, 87:156–160 (1987)) the β-galactosidase gene is driven by the promiscuous (i.e. non-tissue specific) MLV promoter in the U3 region of the LTR (FIG. 3). According to one embodiment the present invention a derivative of the BAG vector has been constructed in which the MLV promoter (U3) located within the 3'LTR (FIG. 3) has been deleted and replaced with a polylinker, said polylinker allowing the facile introduction of heterologous promoters. The BAG vector lacking the U3 is expressed from the MLV promoter (U3) within the 5'LTR when introduced into a packaging cell line. As a result of the rearrangements occurring in the retroviral genome during its life cycle, following infection of its target cell, the polylinker will be duplicated at both ends of the retroviral genome as described above. Thereby a retroviral vector can be constructed in which the expression of the β-galactosidase gene of BAG will be controlled by the polylinker or any promoter inserted into the polylinker in the target cell (FIG. 3).

Further, the replacement of β-galactosidase with a therapeutic gene such as one, encoding melittin, cecropin or another antimicrobial peptide will result in a retroviral vector that can be manipulated to express this gene from any inserted promoter.

Procon vectors carrying tissues specific promoters and regulatory elements such as the Tat Responsive Element (TAR) from HIV will be useful for directing the expression of the therapeutic naturally occurring antimicrobial peptide sequences or derivatives thereof to predefined cell types, tissues and organs. Potential therapeutic sequences include mellitin, which has anti-HIV and anti-tumour effects, cecropin and megainin sequences and sequences which prime cells for death including the thymidine kinase, guanine phosphoribosytransferase and cytosine deaminase genes.

DETAILED DESCRIPTION OF THE INVENTION

The following examples will illustrate the invention further. These examples are however in no way intended to limit the scope of the present invention as obvious modifications will be apparent, and still other modifications and substitutions will be apparent to any skilled in the art.

The recombinant DNA methods employed in practicing the present invention are standard procedures, well known to those skilled in the art, and described in detail, for example, in Molecular Cloning, Sambrook, et al., Cold Spring Harbor Laboratory, (1989) and B. Perbal, A Practical Guide to Molecular Cloning, John Wiley & Sons (1984).

EXAMPLES

Construction of Retroviral Vectors Carrying the PreProCecropin A Sequence

Construction of p125gal

Figure 1:
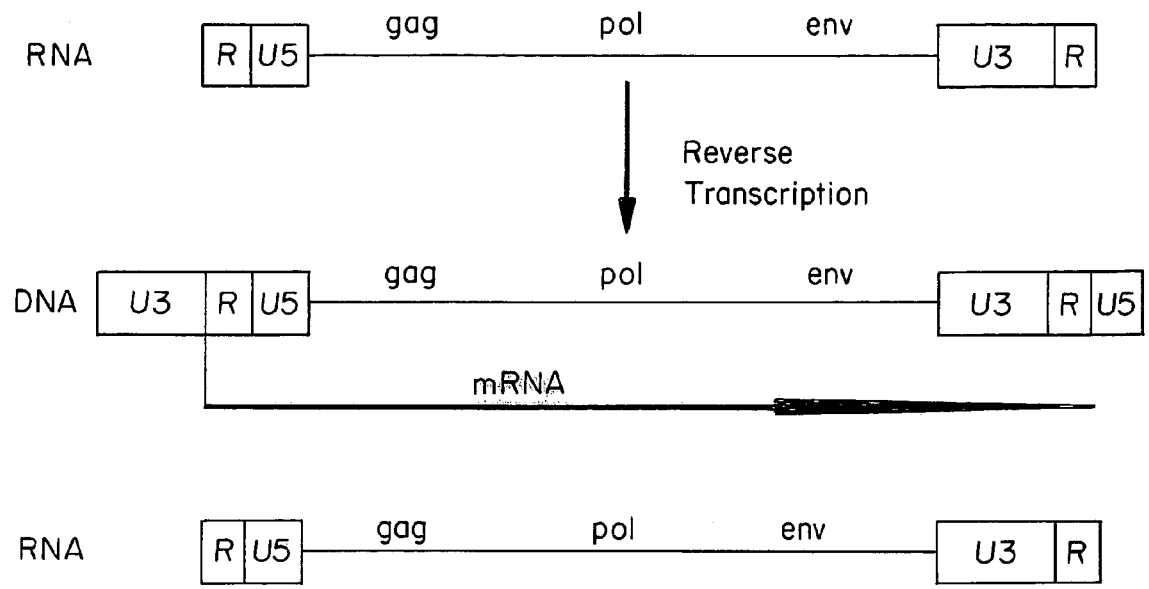
FIG. 1 is a schematic of the mode of reverse transcription of a retrovirus.
Figure 2:
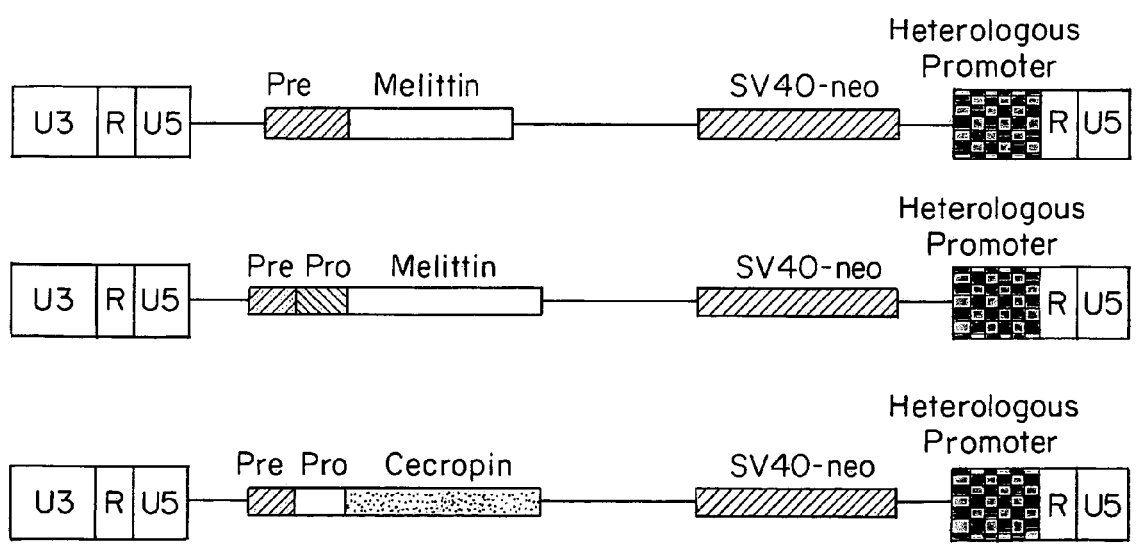
FIG. 2 is a schematic of retroviral vector constructs carrying melittin and cecropin coding sequences.
Figure 3:
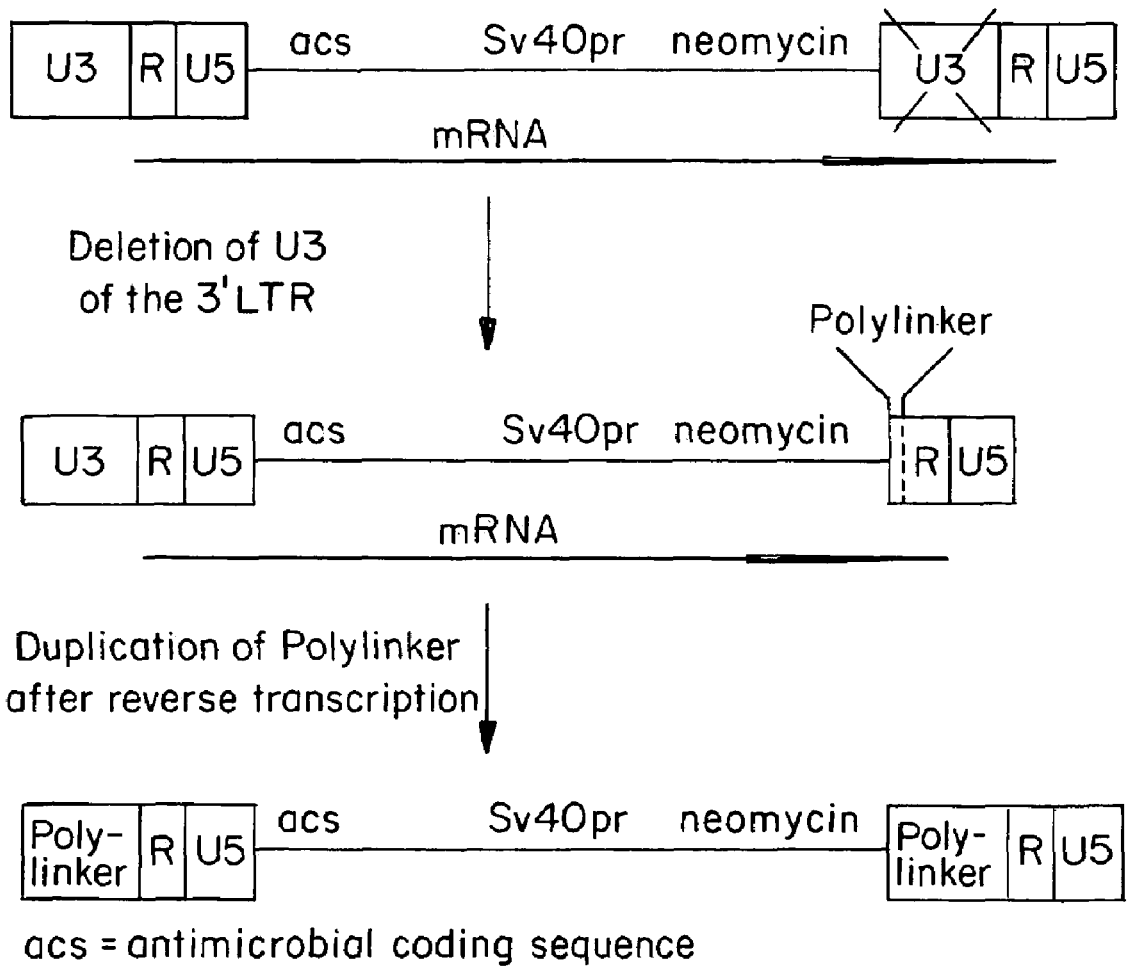
FIG. 3 is a schematic of the construction of U3 minus BAG-vector (MLV).

In the Murine Leukemia Virus (MLV) retroviral vector known as BAG (Price, J. et al., *Proc. Natl. Acad. Sci. USA*, 87:156–160 (1987)) the β-galactosidase gene is driven by the promiscuous (i.e. non-tissue specific) MLV promoter in the U3 region of the LTR (FIG. 3). A derivative of the BAG vector has been constructed in which the MLV promoter (U3) located within the 3'LTR (FIG. 3) has been deleted by PCR. At this position a polylinker was inserted containing the restriction sites SacII and MluI allowing the facile introduction of heterologous promoters. The BAG vector lacking the U3 is expressed from the MLV promoter (U3) within the 5'LTR when introduced into a packaging cell line. As a result of the rearrangements occurring in the retroviral genome during its life cycle, following infection of its target cell, the polylinker will be duplicated at both ends of the retroviral genome as described in Danish patent application no. 1017/94. Thereby a retroviral vector can be constructed in which the expression of the β-galactosidase gene of BAG will be controlled by the polylinker or any promoter inserted into the polylinker in the target cell (FIG. 3).

Figure 4A:
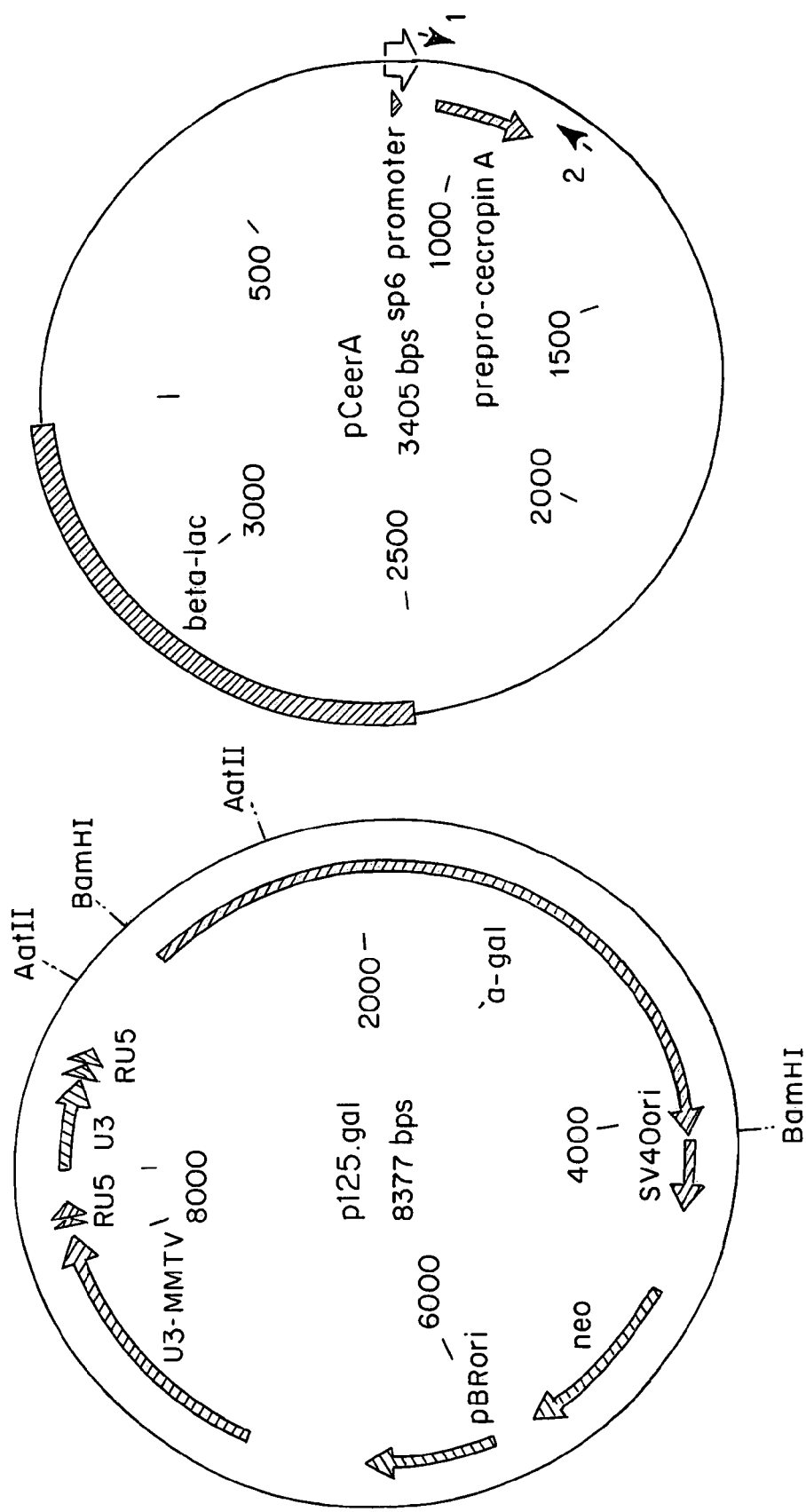
FIGS. 4A–4C are schematics of the construction of the retroviral vector p125.Cecr.A carrying the PreProCecropin A gene.

The Mouse Mammary Tumour Virus (MMTV) U3-region (mtv-2) without the inverted repeats, which contains the MMTV promoters as well as a region that confers responsiveness to glucocorticoid hormones and a region containing an element that directs expression to the mammary gland was inserted into the polylinker region of the modified BAG vector to produce p125gal (FIG. 4A).

Construction of p125CecrA

Figure 4B:
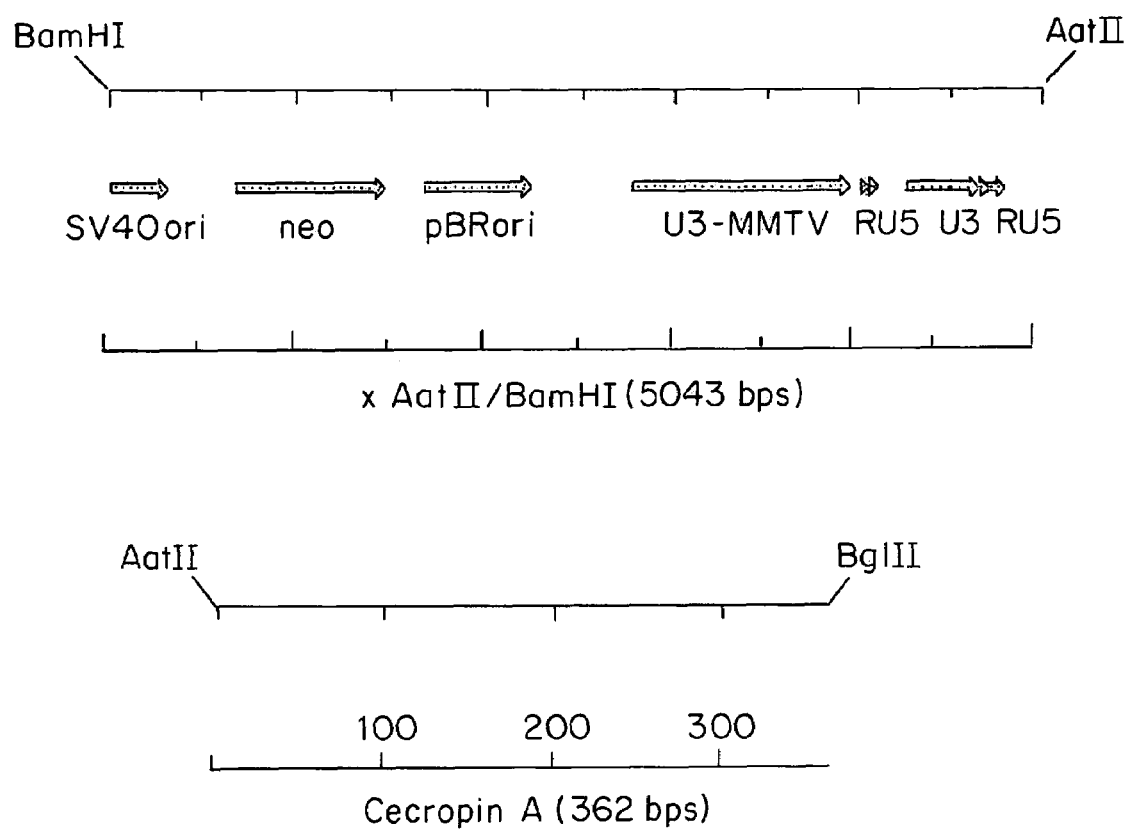
Figure 4C:
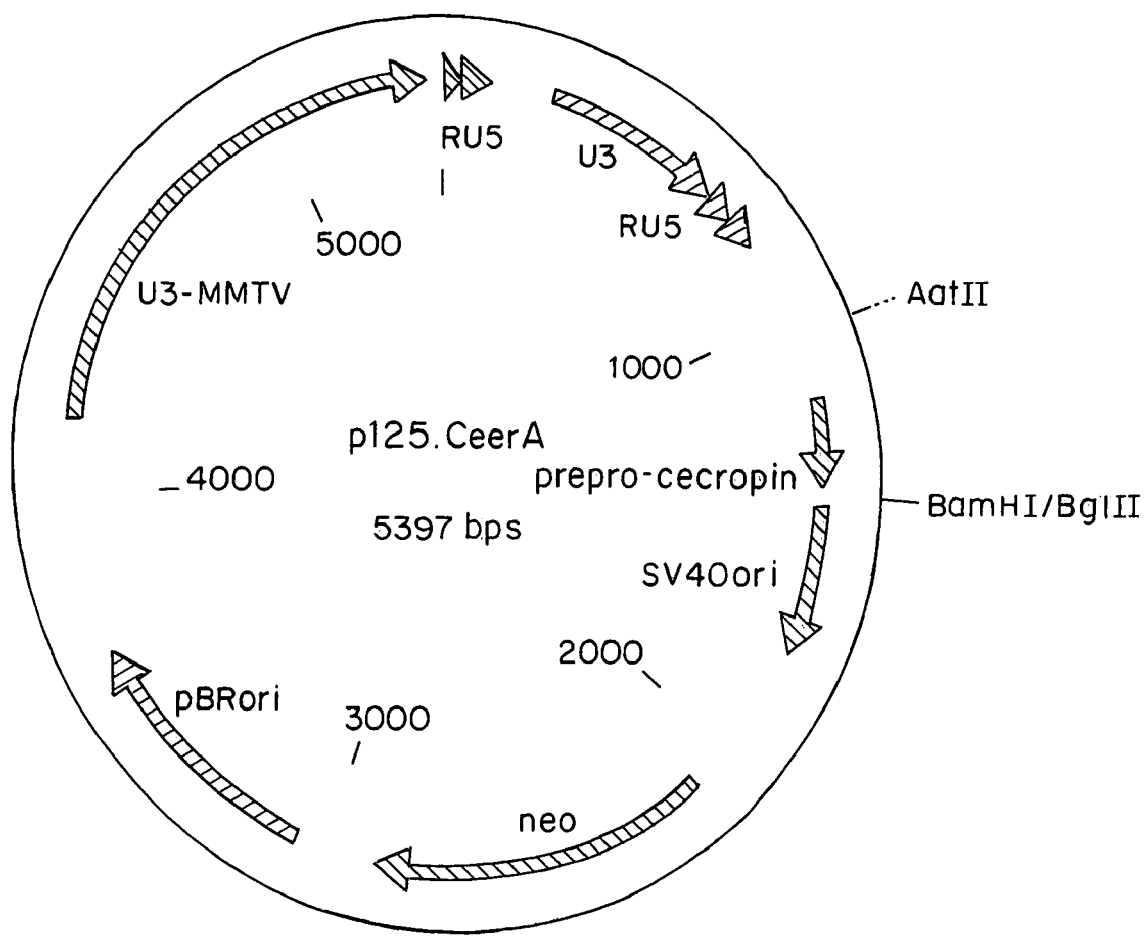

FIGS. 4A–4C illustrate the construction of the retroviral vector p125CecrA. The plasmid pCecrA (obtained from Boman, H. G. et al., *Ann. Rev. Immunol.*, 13:1–51 (1995))

and illustrated in FIG. 4A carries the cDNA of the PrePro-Cecropin A gene from the giant silk moth (*Hyaophora cecropia*) cloned in front of the bacterial sp6 promoter. The PreProCecropin sequence was obtained by amplification by PCR from this plasmid using the following

```
primers:
Primer 1: CecrA1 5'-TATGACGTC-TCGTTAGAACGCGGCT-3'    (SEQ ID NO: 3)
Primer 2: CecrA3 5'-GGCAGATCT-TAAATGTATCATGCAAT-3'   (SEQ ID NO: 4)
```

CecrA1 carries an Aatll restriction site (GACGTC) (SEQ ID NO: 5) in the 5' extension with a 3 base pair protection (TAT). Similarly CecrA3 carries a Bglll site (AGATCT) (SEQ ID NO: 6) in the 5' extension with a 3 base pair protection (GGC).

The PCR product (370 bps) was then digested with Aatll and Bglll to make the restriction sites available for cloning (FIG. 4B).

P125gal was digested with the restriction enzymes Aatll and BamHl resulting in a fragment of 5043 base pairs (FIG. 4B) and ligated to the fragment carrying the PreProCecropin A gene from pCercA. This resulted in the formation of p125.CercA (FIG. 4C), the BamHl/Bglll sites being lost.

Figure 5A:
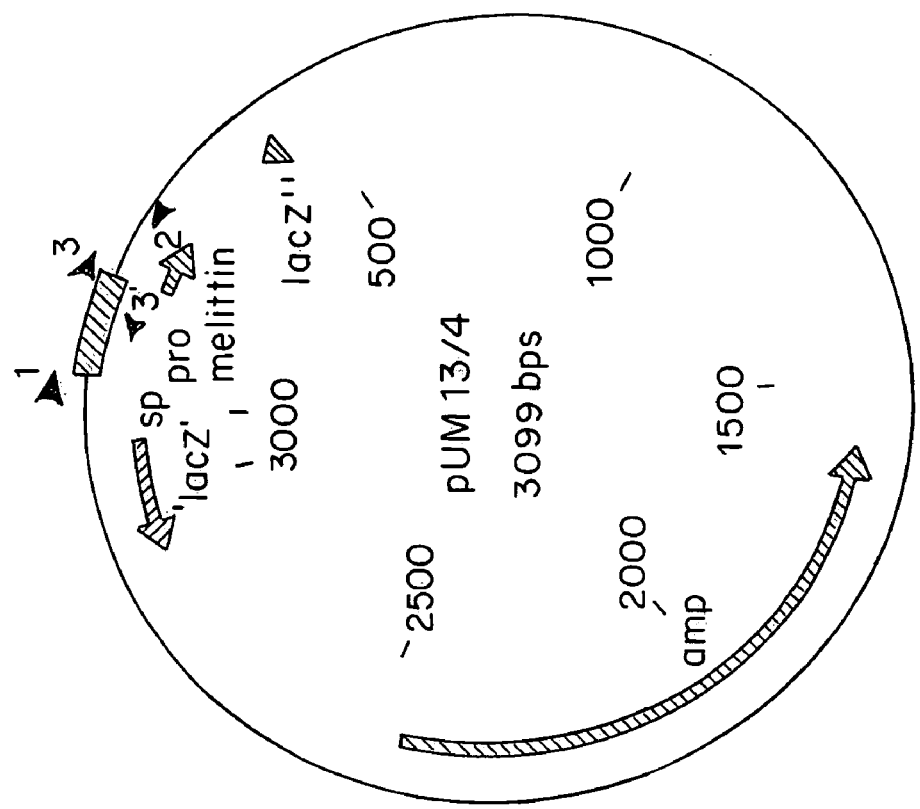
FIGS. 5A–5C are schematics of the construction of the retroviral vectors pBAGpMel and pBAGppMel carrying respectively the PreMelittin and the PreProMelittin gene.
Figure 5A:
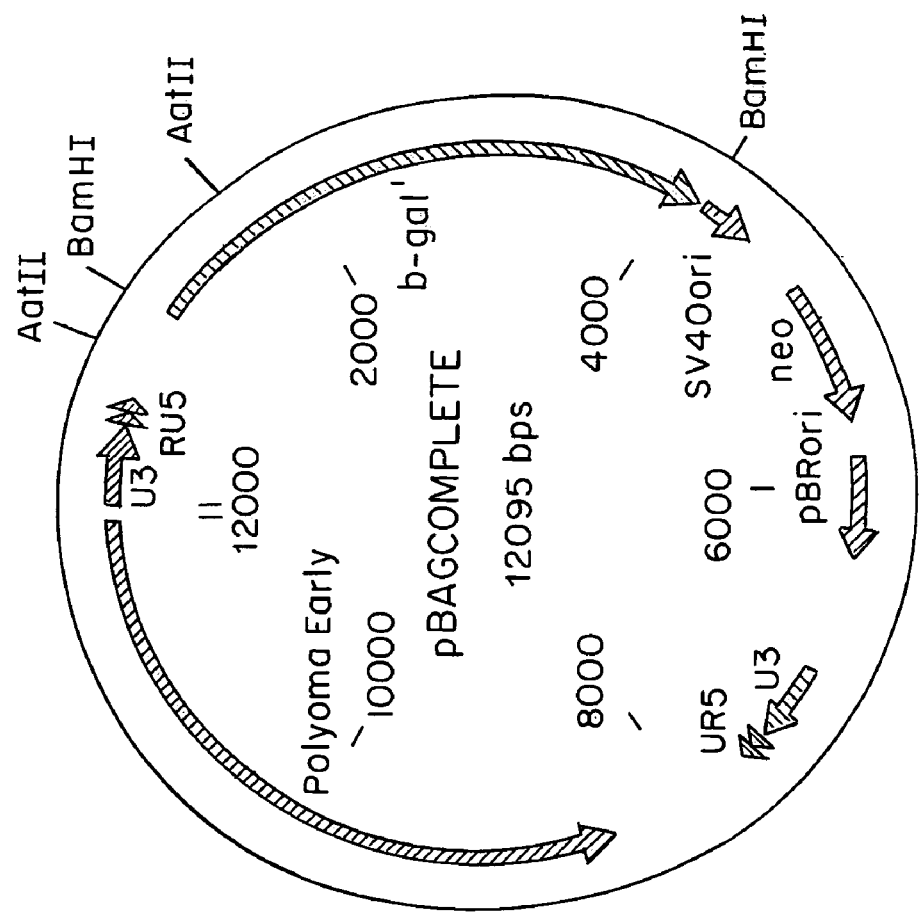
Figure 5B:
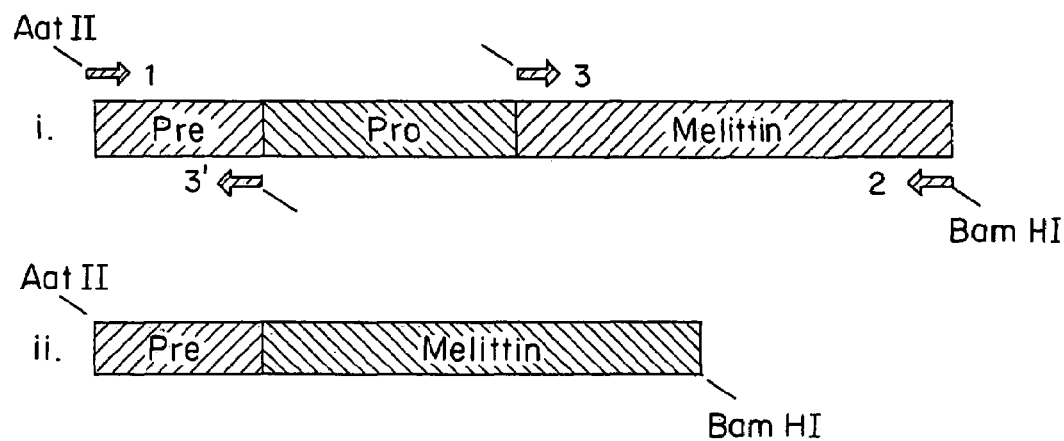
Figure 5C:
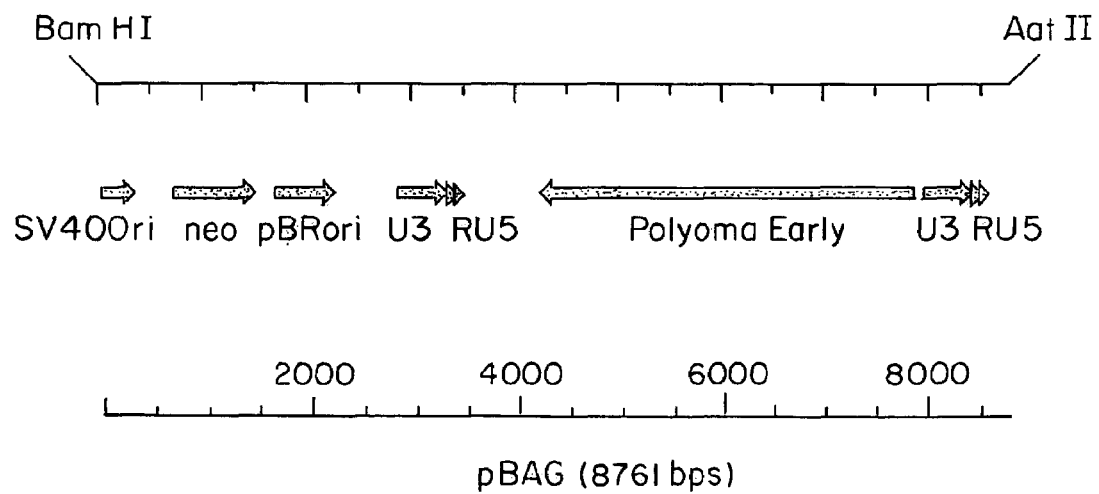

Construction of Retroviral Vectors Carrying the PrePre-Melittin and PreMelittin Sequence FIGS. 5A–5C illustrate the construction of the retroviral vectors pBAGpMel and pBAGppMel. The plasmid pUM13/4 (Vlasak, R., Uger-Ullmann, C., Keil, G. and Frischauf, A-M, *Eur. J. Biochem.*, 135:123–126 (1989)) (FIG. 5A) carries the cDNA encoding the PrePromelittin gene from *apis mellifera*. The PreProMelittin and the Premelittin sequence was obtained by amplification by PCR using the following primers:

```
Primer 1:  5'-ATAGACGTC-AAGGAAGGAAGCGATCGGA-3'         (SEQ ID NO: 7)
Primer 2:  5'-TATGGATCC-AACCCTGTTGCCTCTTACG-3'         (SEQ ID NO: 8)
Primer 3:  5'-TCTTACATCTATGCG-GGAATTGGAGCAGTTCTGAA-3'  (SEQ ID NO: 9)
Primer 3': 5'-AACTGCTCCAATTCC-CGCATAGATGTAAGAAATGT-3' (SEQ ID NO: 10)
```

Primer 1 carries an Aatll site (GACGTC) (SEQ ID NO: 11) in the ≡' extension with an ATA 3 bp protection and primer 2 carries BamHl site (GGATCC) (SEQ ID NO: 12) in the 5' extension with a TAT 3 bp protection.

Figure 6:
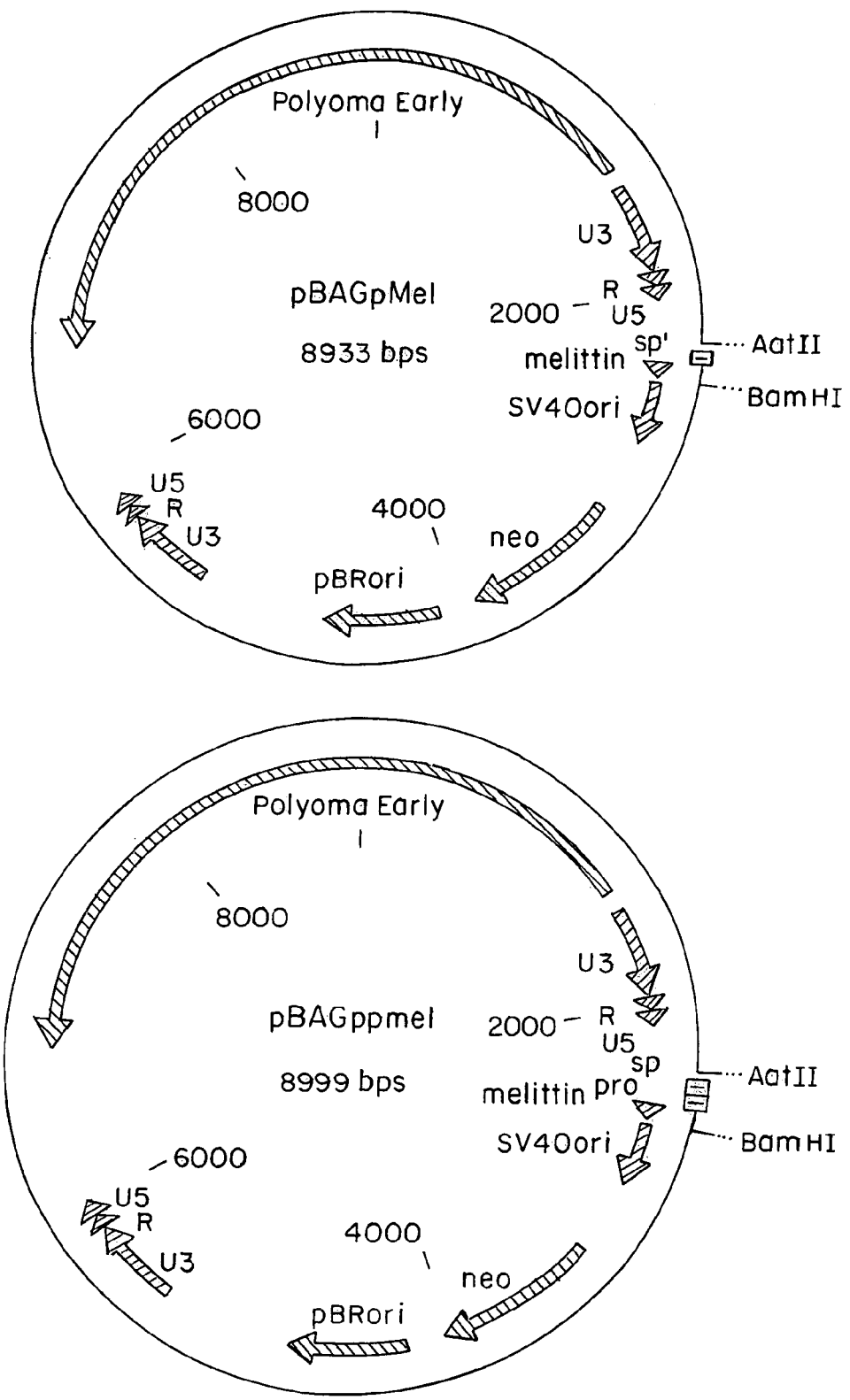
FIG. 6 is a schematic of the pBAGpMel and pBAGppMel.

A PCR on the plasmid pUM13/4 with primers 1 and 2 results in the amplification of the whole PreProMelittin sequence (FIG. 5B) carrying both Aatll and BamHl sites to enable cloning into the retroviral vector pBAG (FIG. 5A) after digestion of the plasmid with Aatll and BamHl (FIG. 5C). The resulting plasmid pBAGppMel is shown in FIG. 6.

The amplification of the PreMelittin sequence was carried out using a combination of conventional PCR and recombinant PCR. Primer 3, though binding in the melittin gene, carries a 5' extension that corresponds to the 3' sequence of the Pre sequence. Similarly, the Primer 3', though binding in the 3' region of the Pre sequence, carries a 5' extension corresponding to the sequence in the 5' region of the melittin gene. Initially a PCR was made with either primer pair 1 and 3' or 2 and 3. The products from these two reactions were then used to make a recombinant PCR. This entailed hybridising the two PCR products with each other using the 5' extensions that were carried in the primers 3 and 3'. Subsequent addition of primers 1 and 2, which adds the Aatll and BamHl sites for cloning into pBAG allowed the amplification of the entire PreMelittin sequence (FIG. 5B). Plasmid pBAGpMel (FIG. 6) was produced by digestion of this PCR product and pBAG with Aatll and BamHl followed by ligation of the fragments.

Isolation of Clones

EJ cells were transfected with p125.CercA and the clones expressing neomycin resistance were isolated. Six clones were isolated: Cecropin A1.4, Cecropin A1.7, Cecropin A1.8, Cecropin A10.3, Cecropin A10.4, and Cecropin A10.8.

Similarly Ej cells were transfected with pBAGpMel and pBagppMel and the clones expressing neomycin resistance were isolated. Three clones containing the premelittin gene were isolated: Pre Melittin 1, Pre Melittin 4, and Pre Melittin 6. Two clones containing prepromelittin were isolated: Pre Pro Melittin 1, and Pre Pro Melittin 5.

S1 Analysis of Transfected Cecropin/Melittin Clones

Figure 7:
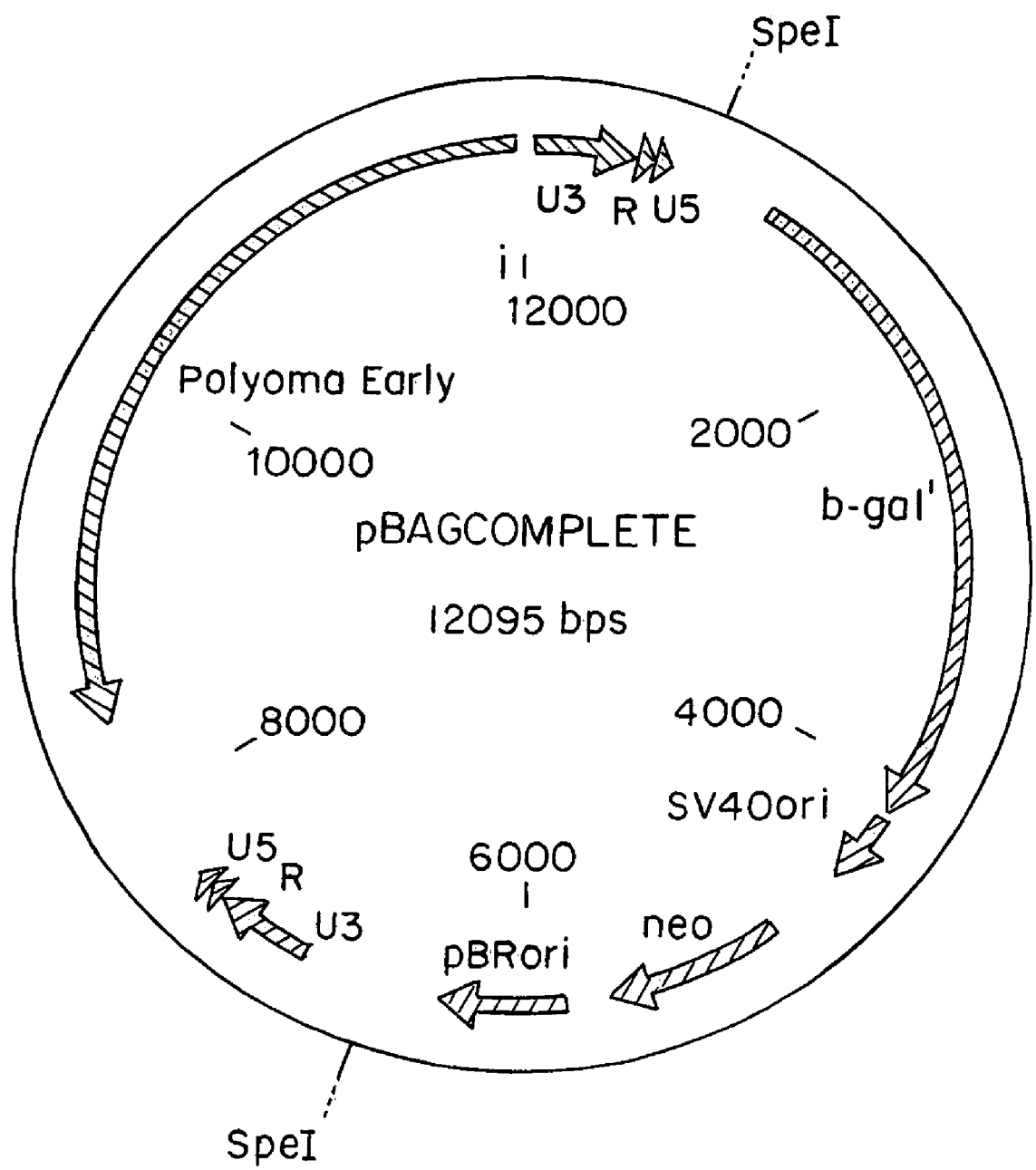
FIG. 7 is a schematic of the pBAG.
Figure 8A:
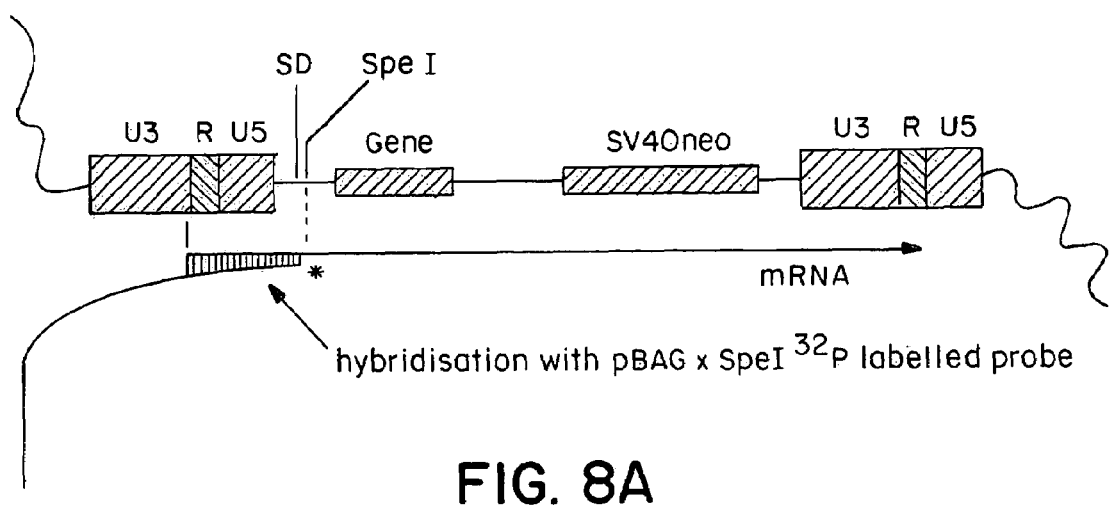
FIGS. 8A–8B are schematics of the principle of S1 analysis of transfected Cecropin and Melittin clones.

An S1 analysis was performed using pBAG digested with Spel as a probe (FIG. 7), the resulting 6.1 kb fragment comprising 3'LTR, polyoma early region and 5'LTR. The fragment was then end-labeled using polynucleotide kinase with 32P and hybridized against total RNA isolated from Ej (human bladder carcinoma cell line) cell clones that had been transfected with retroviral vector constructs bearing either preprocecropin (clones A1.4, A1.7, A1.8, A10.4, A10.3, and A10.8), premelittin (clones 1, 4 and 6), and prepromelittin (clones 1 and 5) or the empty vector alone (pBAG clones 3 and 6) (FIG. 8A).

Figure 8B:
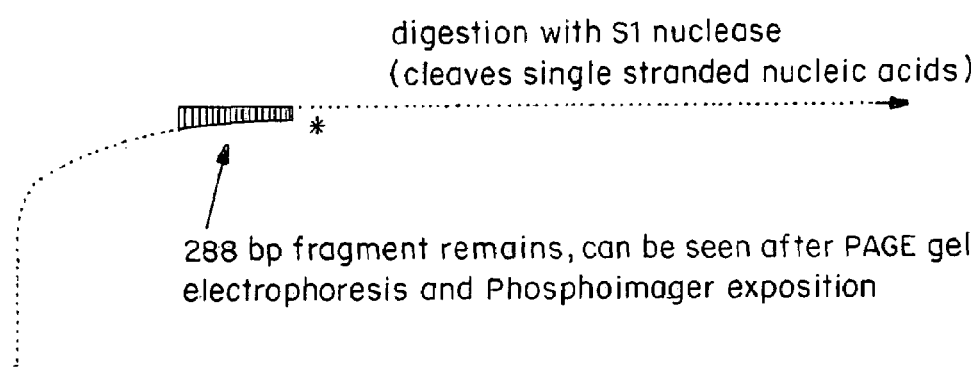
Figure 9A:
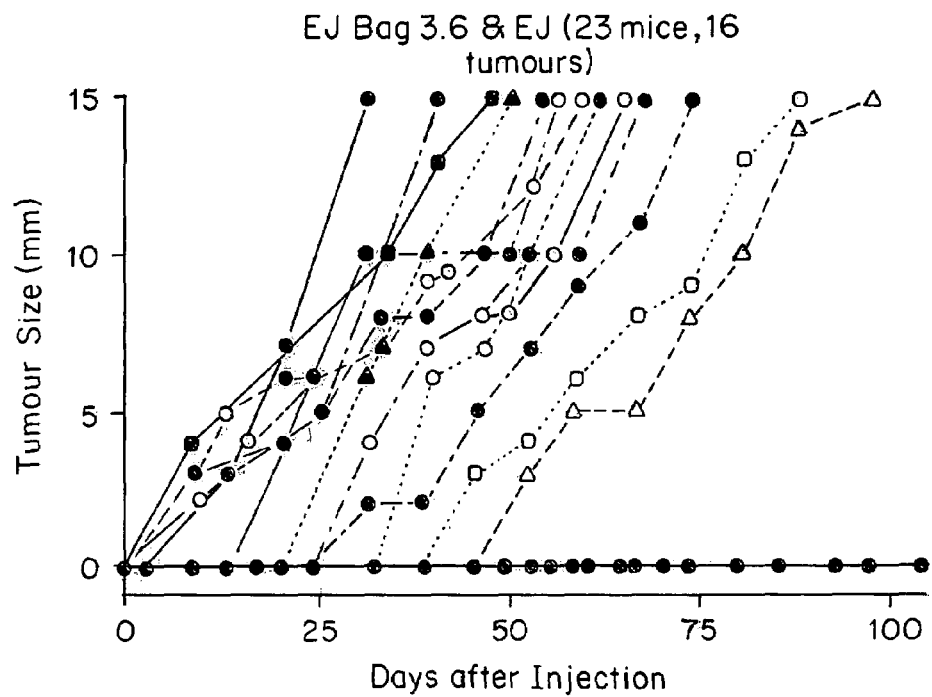
FIGS. 9A–9G are graphs of days after injection versus tumor site showing antitumour activity of retroviral vectors carrying PreProCecropin coding sequences.
Figure 9B:
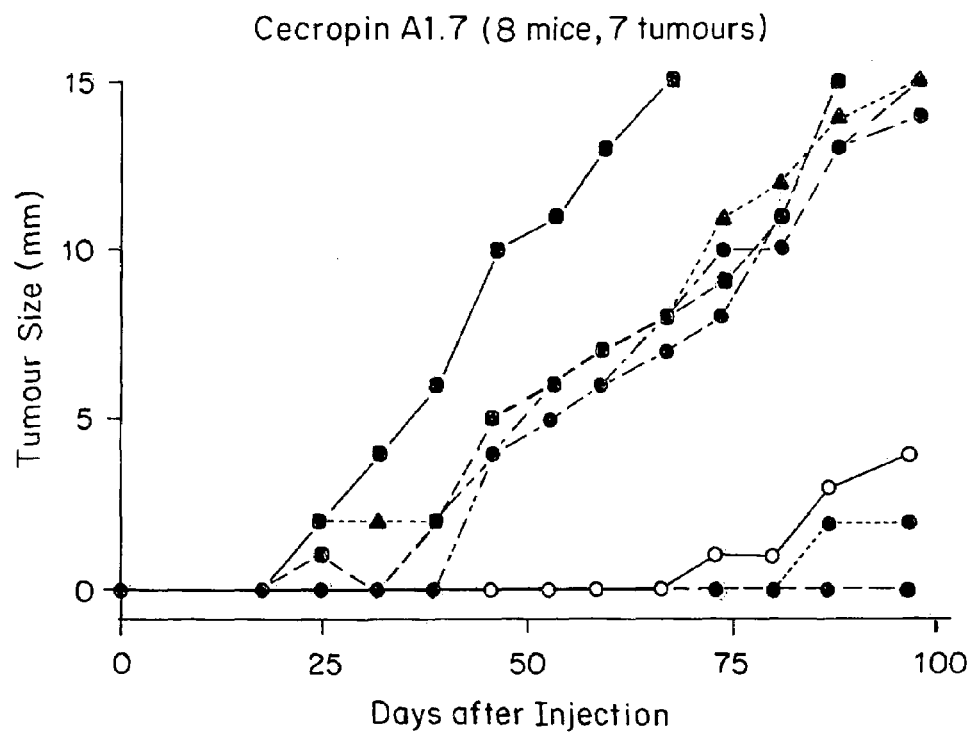
Figure 9C:
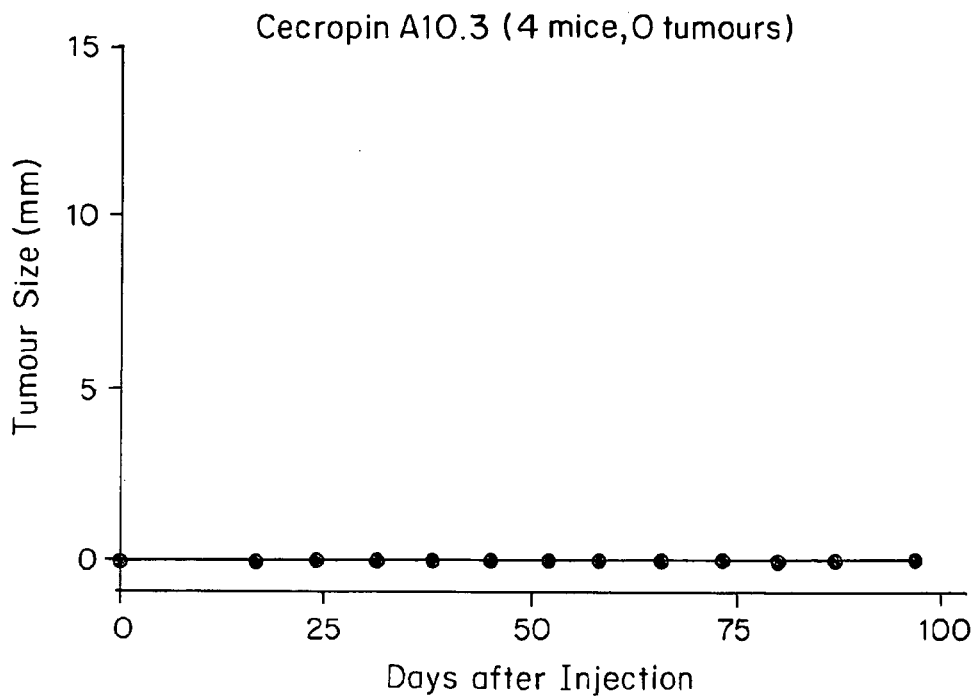
Figure 9D:
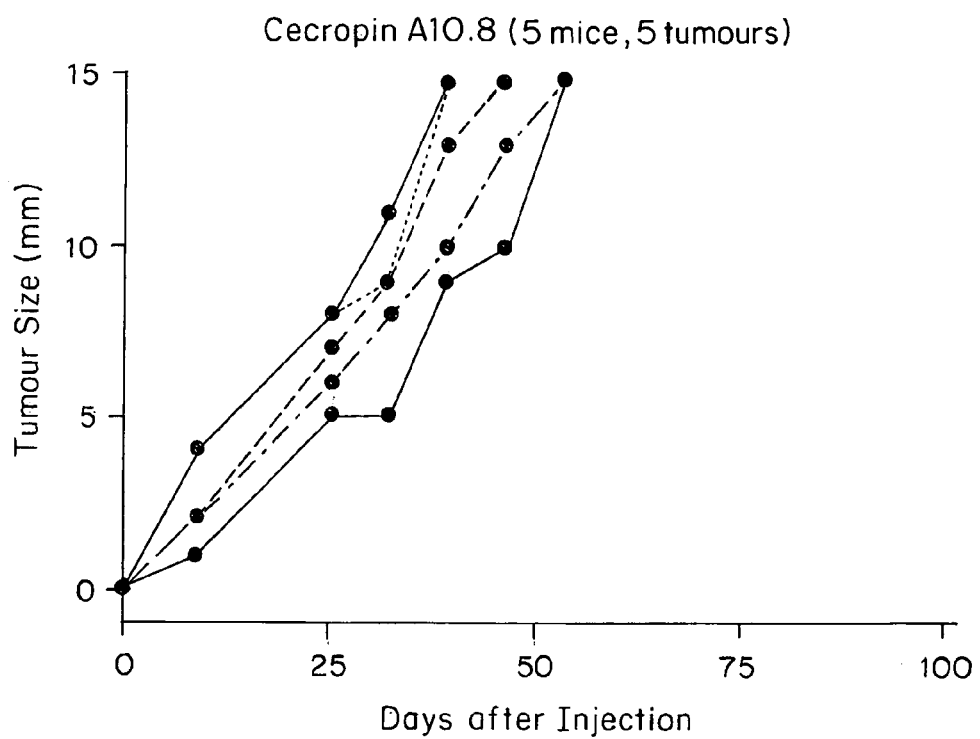
Figure 9E:
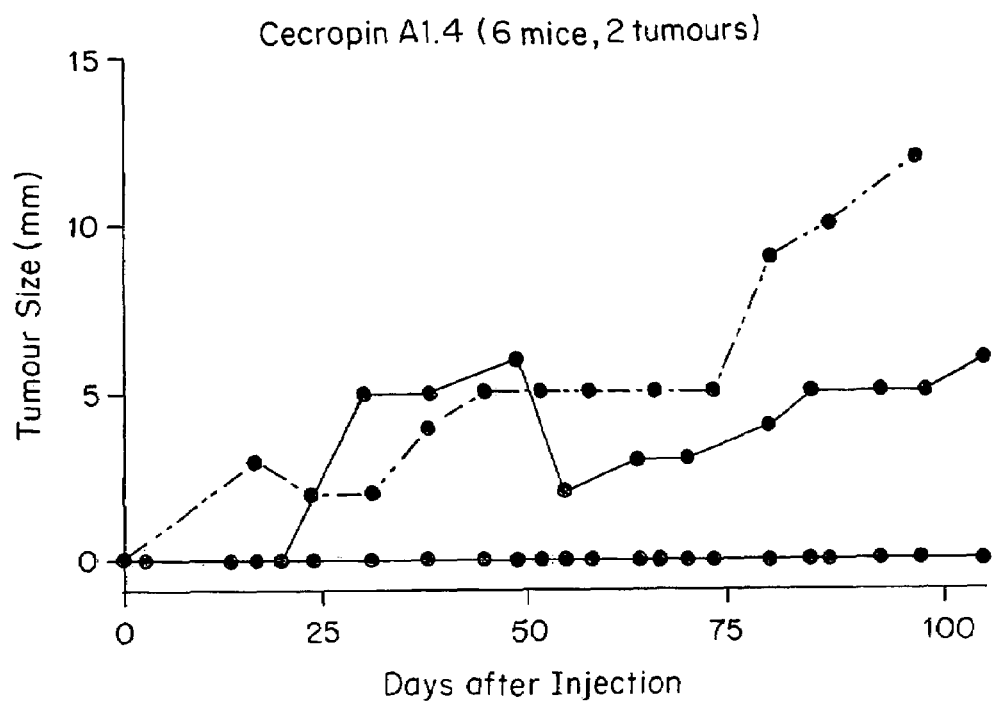
Figure 9F:
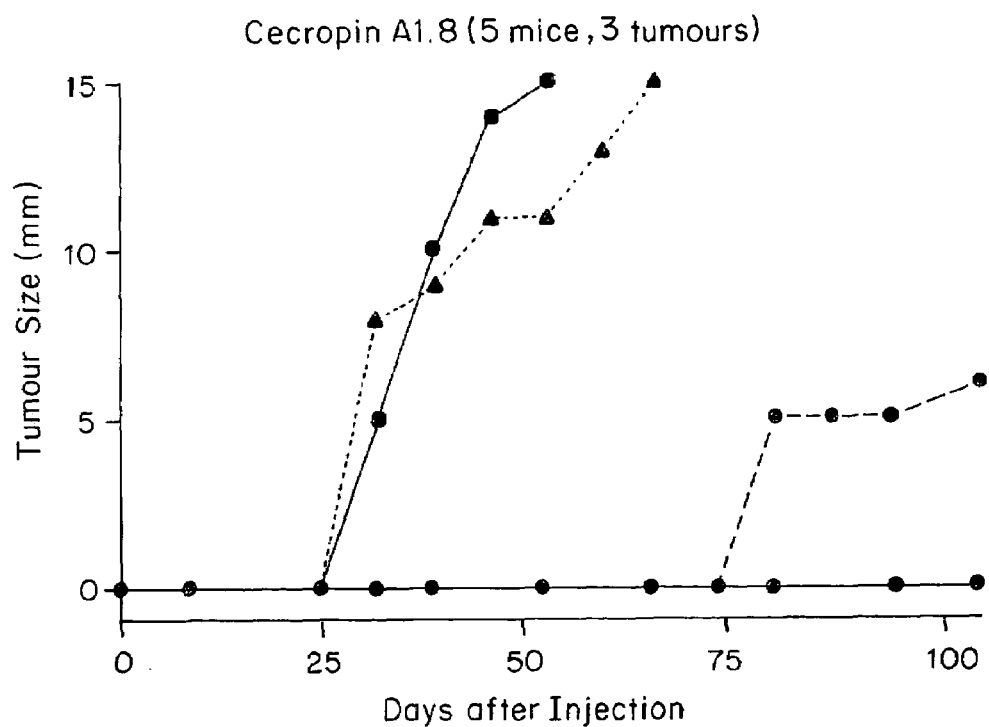
Figure 9G:
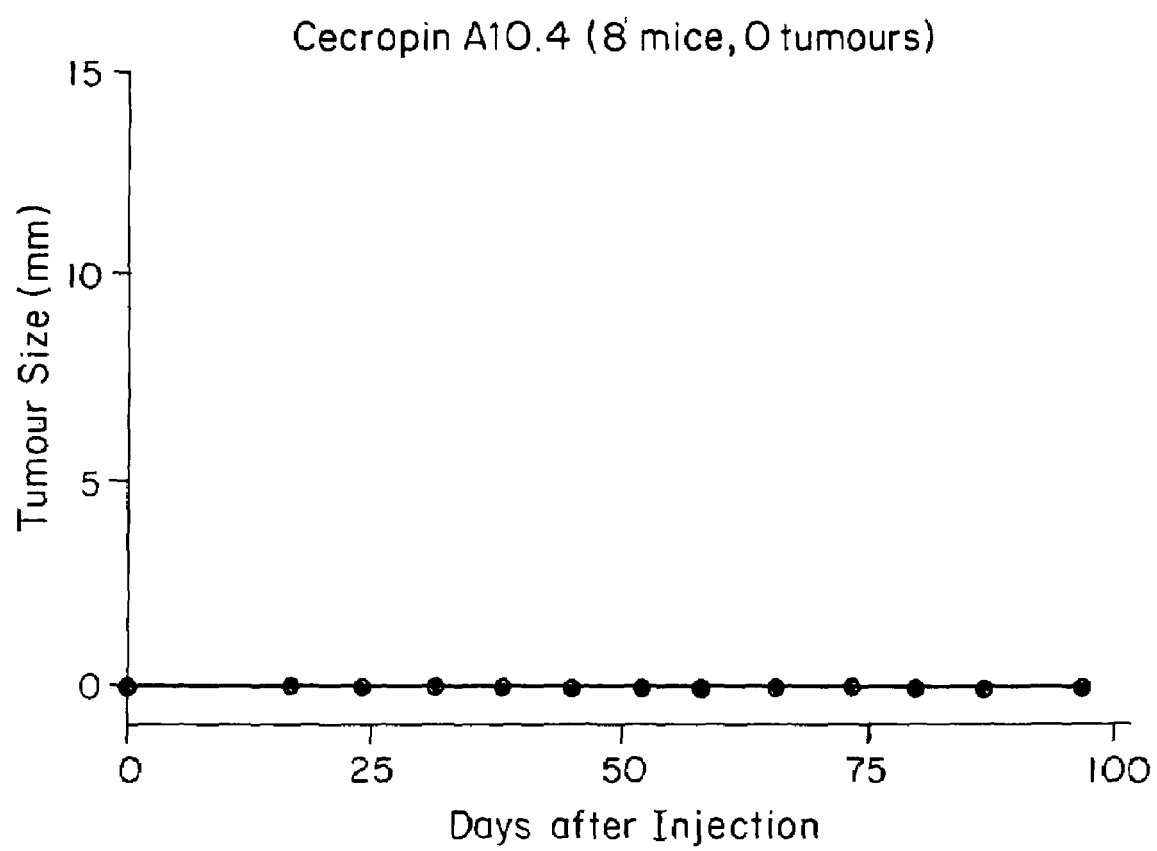
Figure 10A:
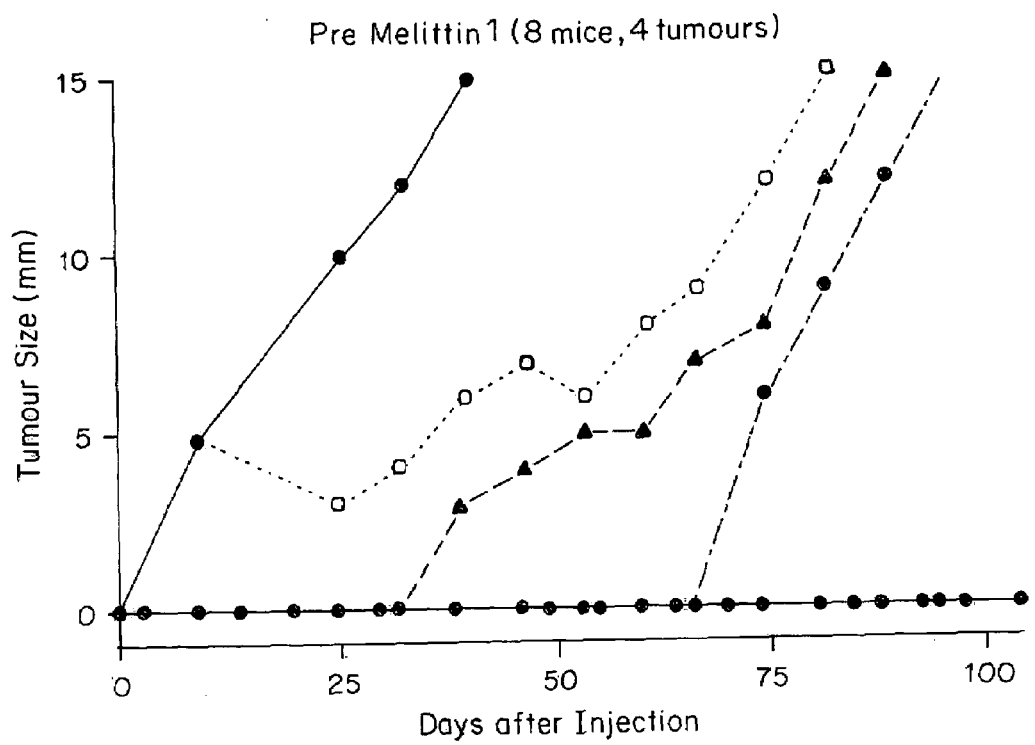
FIGS. 10A–10F are graphs of days after injection versus tumor site showing antitumour activity of retroviral vectors carrying Melittin coding sequences.
Figure 10B:
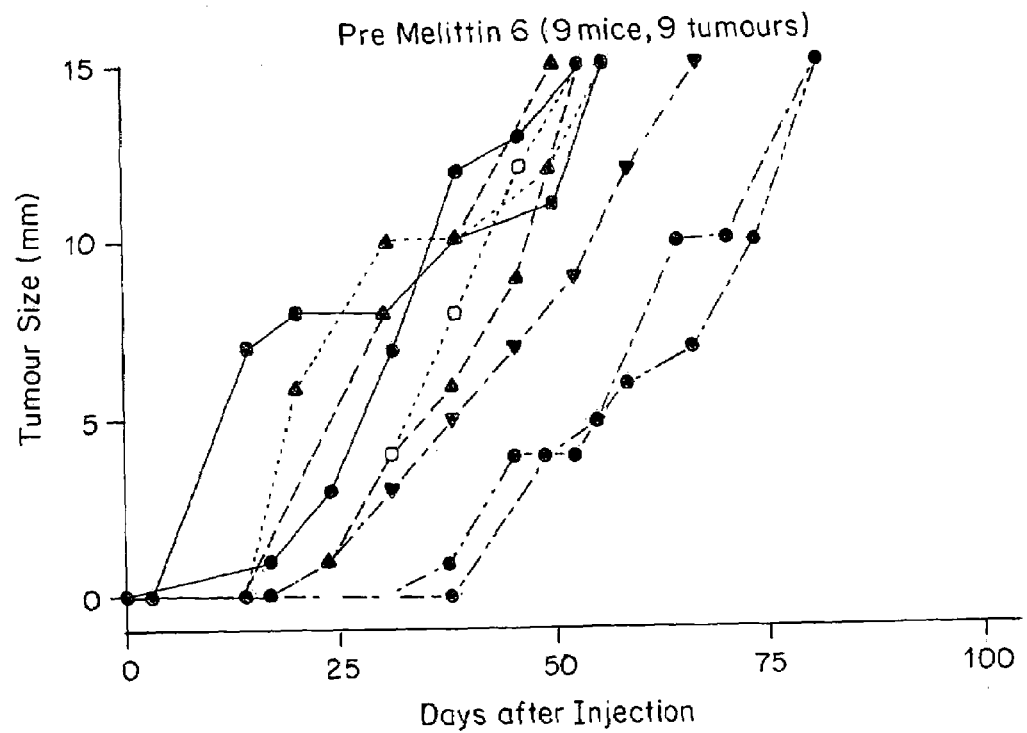
Figure 10C:
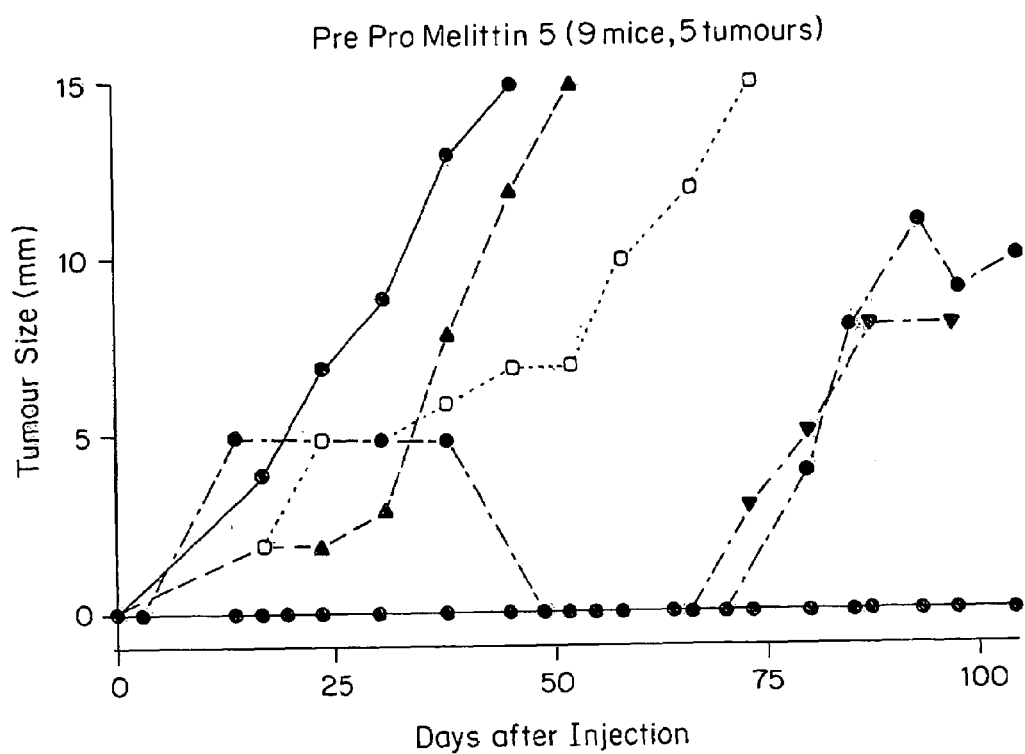
Figure 10D:
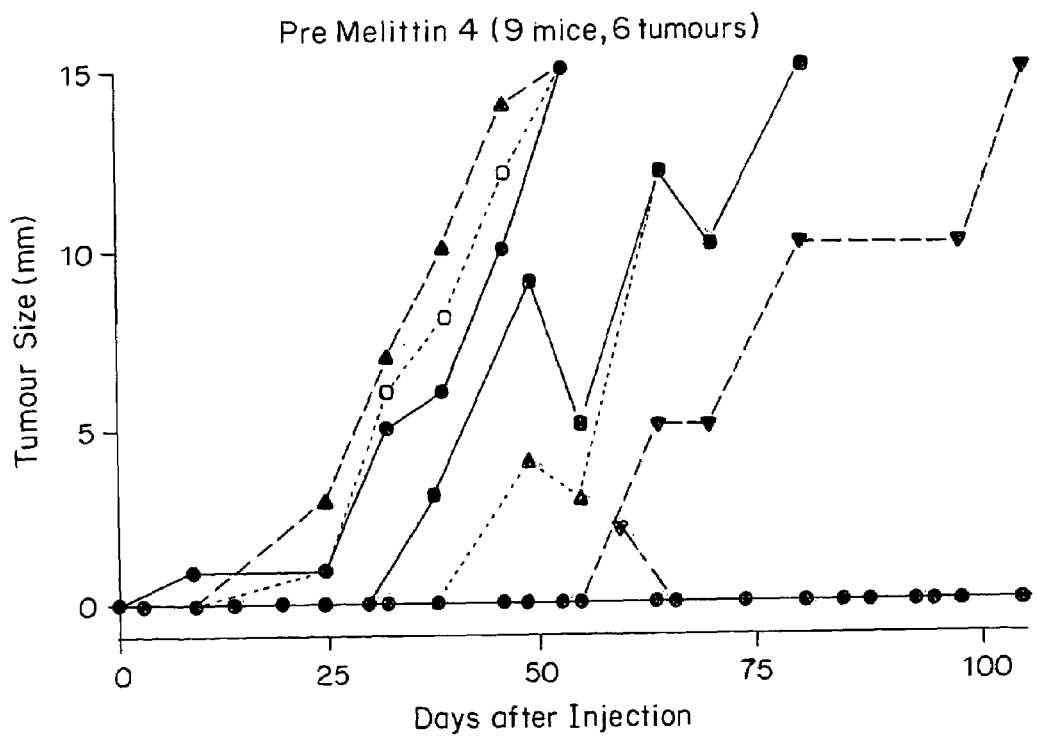
Figure 10E:
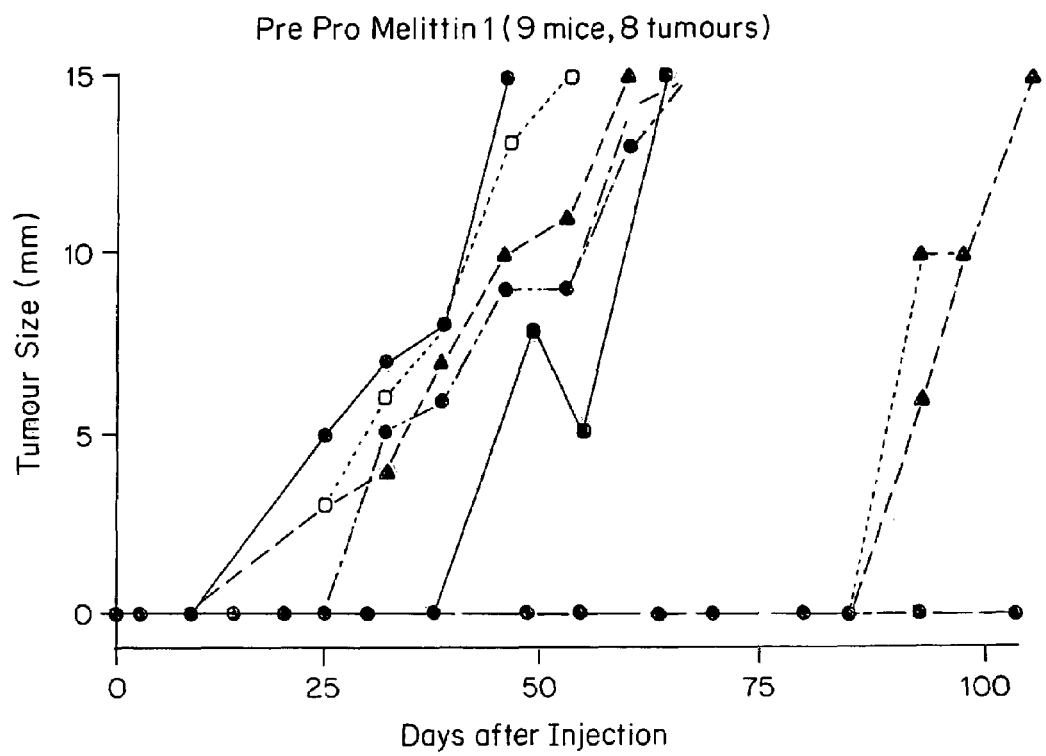
Figure 10F:
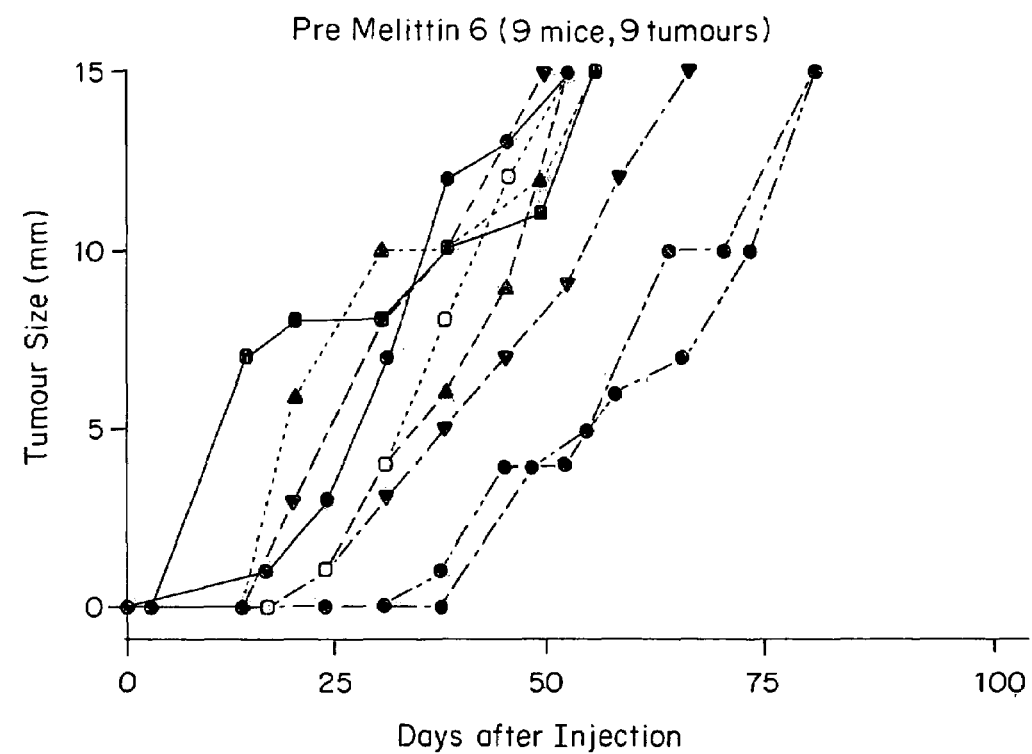

There followed an S1 nuclease digestion (FIG. 8B), the enzyme cleaving only single stranded nucleic acids, resulting in a 288 bp fragment arising from the hybridization of the probe to the mRNA coming from the retroviral vector that is present in the genomic DNA of the transfected clones.

Subsequent separation using a 6% polyacrylamide gel and exposure of the gel using a Phosphor-imaging system (Fuji BAS1000) revealed the expected bands.

Antitumour Experiments

Many amphipathic polypeptides are synthesized in a preproform which is inactive (Boman H. G., *Ann. rev. Immunol.*, 13:1–51 (1995)). The endopeptidase that cleaves of the presignal peptide in a co-translational process is thought to be present in all cells whereas the protease that converts promelittin to the active melittin form appears to be present only in certain cells (Kreil G., et al., *Eur. J. Biochem.*, 111:49–58 (1980)).

The human bladder carcinoma derived cell line, EJ, gives tumours upon injection into immuno compromised nude mice which grow progressively larger (FIGS. 9A–9G). The stable clones of Ej cells carrying the melittin or cecropin expression constructs obtained as described above were tested for their tumorigenicity in nude ice. Generally, cell clones carrying the cecropin, prepromelittin, or premelittin genes show a reduced rate of tumour growth in mice (FIGS. 9A–9G and 10A–10F), i.e. both melittin and cecropin have anti-tumour effects. In a separate experiment the Cecropin A1.4 clone was tested in 4 mice, only of which showed a tumour.

Anti-Viral Activity

Figure 11:
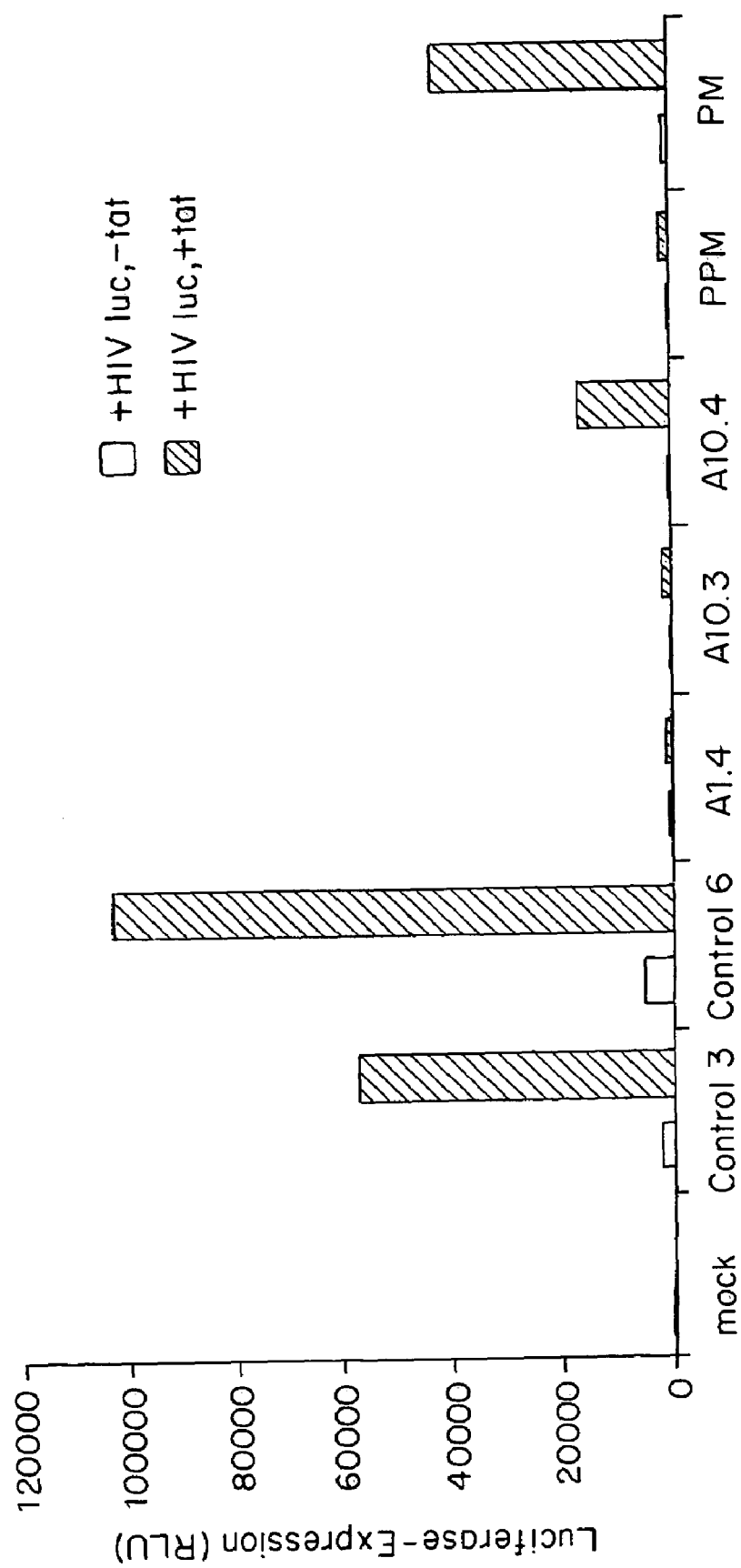
FIG. 11 is a graph showing downregulation of expression from HIV LTR of retroviral vectors carrying Cecropin and Melittin coding sequences.
Figure 12:
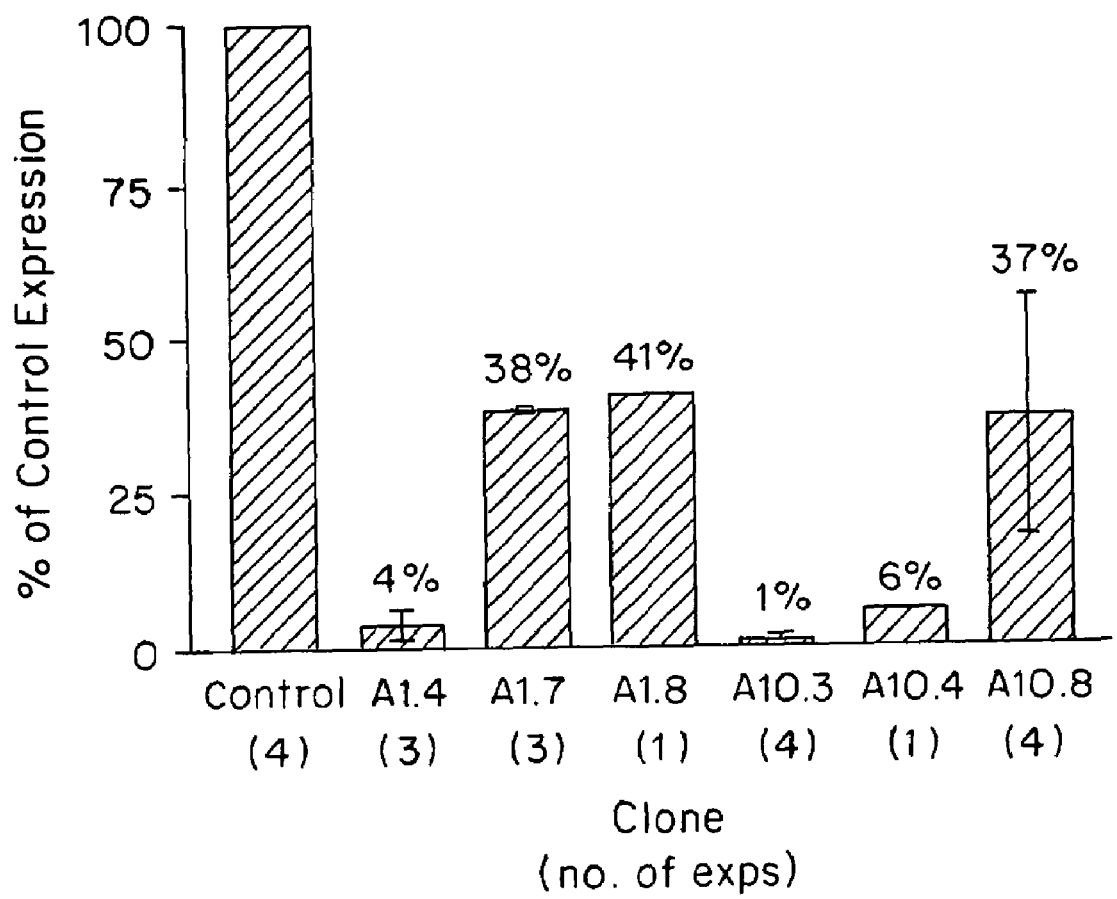
FIG. 12 is a graph showing downregulation of expression of HIV LTR of retroviral vectors carrying Cecropin coding sequences.

EJ derived cell clones carrying the melittin or cecropin expression vector or the parental. BAG vector, not carrying a therapeutic gene, were supertransfected with an indicator construct carrying the HIV LTR (and thus the HIV promoter) linked to a firefly luciferase reporter gene (HIV-luc) in the absence or presence of a separate construct expressing Tat. In the absence of Tat there was little luciferase activity detectable from the HIV-luc construct in all cell clones as expected since the HIV promoter requires Tat for its activity. In contrast, in the presence of Tat, cell clones carrying BAG or a premelittin carrying construct show significant levels of luciferase expression, whereas a cell clone transfected with either a prepromelittin or a cecropin expression construct showed little luciferase expression (FIGS. 11 and 12). This suggests that cecropin, prepromelittin and to a lesser extent premelittin inhibit the Tat driven expression from the HIV LTR. Thus the production of HIV from infected cells will be inhibited by the antimicrobial peptide gene carrying therapeutic-retroviral vector. This effect is expected to lead to a lack of virus production from HIV infected cells.

Figure 13A:
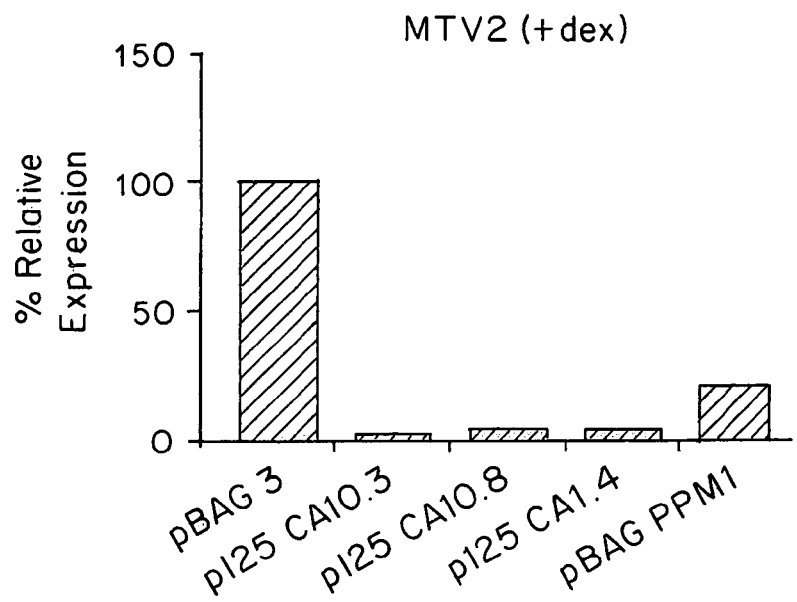
FIGS. 13A–13B are graphs showing downregulation of LTR's from Mouse Mammary Tumour Virus (MMTV) be retroviral vectors carrying Cecropin and Melittin coding sequences.
Figure 13B:
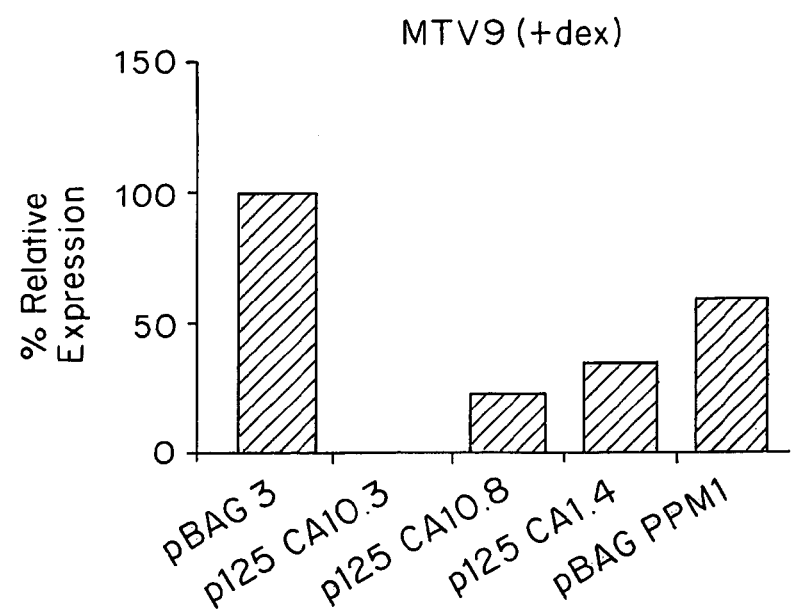

A similar experiment to that of FIGS. 11 and 12 can be seen in FIGS. 13A–13B whereby two different MMTV LTR's controlling the expression of a luciferase reporter gene (Wintersberger et al., *Proc. Natl. Acad. Sci. USA*, 92:2745–2749) were separately supertransfected into cells carrying either PreProCecropin or PreProMelittin under control of an MLV promoter. These experiments showed that the downregulatory effect of Cecropin is not restricted to the HIV promoter, but also work with another retroviral vector.

In conclusion the present invention provides therapeutic products for the treatment of retroviral infections including HIV, tumours, bacterial and viral infections comprising vector constructs carrying genes or derivatives thereof of therapeutic active peptides including those for melittins, cecropins and magainins.

Equivalents

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. A recombinant retroviral vector system comprising:
   (a) A recombinant vector comprising,
      (i) a 5' long terminal repeat region comprising the structure U3-R-U5;
      (ii) one or more coding sequences, said sequences being inserted into the body of the vector outside of the 5' and a 3' long terminal repeat regions, wherein at least one sequence encodes for at least one therapeutic antimicrobial peptide, wherein the antimicrobial peptide is selected from the group consisting of: melittin, cecropin, magainin, a preform thereof, a preproform thereof, a biologically active analogue thereof having antimicrobial activity, and a combination thereof; and
      (iii) a 3' long terminal repeat region comprising a completely or partially deleted U3 region, wherein said deleted U3 region is replaced by a polylinker sequence which comprises at least one unique restriction site and at least one insertion of a heterologous DNA fragment, wherein the heterologous DNA fragment regulates the expression of at least one of the coding sequences of said vector, and comprises one or more elements selected from the group consisting of: regulatory elements and promoters,
      wherein after infection of a target cell, the U3 region of said 5' long terminal repeat region is replaced by said polylinker sequence, resulting in at least one of said coding sequences becoming operatively linked to said heterologous DNA fragment and said heterologous DNA fragment regulating the expression of at least one of said coding sequences in said target cell; and
   (b) a packaging cell line harboring at least one retroviral construct coding for proteins required for said recombinant vector to be packaged.

2. A retroviral particle produced by the recombinant retroviral vector system according to claim 1.

3. A retroviral provirus produced by infection of target cells with a recombinant retroviral particle according to claim 2 whereby the U3 region is duplicated during the process of reverse transcription in the infected target cell and appears in the 5' long terminal repeat and the 3' long terminal repeat of the resulting provirus, and the U5 of the 5' long terminal repeat is duplicated during the process of reverse transcription in the infected target cell and appears in the 3' long terminal repeat and in the 5' long terminal repeat of the resulting provirus.

4. A method for introducing nucleotide sequences into an isolated cell population comprising infecting the cell population with the retroviral particle according to claim 2.

5. The method of claim 4 wherein the cell population is selected from the group consisting of: human cells and animal cells.

6. A mRNA of a retroviral provirus produced by infection of target cells with a recombinant retroviral particle from a recombinant retroviral vector system comprising:
   (a) a recombinant vector comprising,
      (i) a 5' long terminal repeat region comprising the structure U3-R-U5;
      (ii) one or more coding sequences, said sequences being inserted into the body of the vector outside of the 5' and a 3' long terminal repeat regions, wherein at least one sequence encodes for at least one therapeutic antimicrobial peptide, wherein the antimicrobial peptide is selected from the group consisting of: melittin, cecropin, magainin, a preform thereof, a preproform thereof, a biologically active analogue thereof having antimicrobial activity, and a combination thereof; and
      (iii) a 3' long terminal repeat region comprising a completely or partially deleted U3 region wherein said deleted U3 region is replaced by a polylinker sequence which comprises at least one unique restriction site and at least one insertion of a heterologous DNA fragment, wherein the heterologous DNA fragment regulates the expression of at least one of the coding sequences of said vector, and comprises one or more elements selected from the group consisting of: regulatory elements and promoters,
      wherein after infection of a target cell, the U3 region of said 5' long terminal repeat region is replaced by said polylinker sequence, resulting in at least one of said coding sequences becoming operatively linked to said heterologous DNA fragment and said heterologous DNA fragment regulating the expression of at least one of said coding sequences in said target cell; and
   (b) a packaging cell line harboring at least one retroviral construct coding for proteins required for said recombinant vector to be packaged.

7. A RNA produced by a recombinant retroviral vector wherein said vector comprises,
   (a) a 5' long terminal repeat region comprising the structure U3-R-U5;
   (b) one or more coding sequences, said sequences being inserted into the body of the vector outside of the 5' and a 3' long terminal repeat regions, wherein at least one sequence encodes for at least one therapeutic antimicrobial peptide, wherein the antimicrobial peptide is selected from the group consisting of: melittin, cecropin, magainin, a preform thereof, a preproform thereof, a biologically active analogue thereof having antimicrobial activity, and a combination thereof; and
   (c) a 3' long terminal repeat region comprising a completely or partially deleted U3 region wherein said deleted U3 region is replaced by a polylinker sequence which comprises at least one unique restriction site and at least one insertion of a heterologous DNA fragment, wherein the heterologous DNA fragment regulates the expression of at least one of the coding sequences of said vector, and comprises one or more elements selected from the group consisting of: regulatory elements and promoters, wherein after infection of a target cell, the U3 region of said 5' long terminal repeat region is replaced by said polylinker sequence, resulting in at least one of said coding sequences becoming operatively linked to said heterologous DNA fragment and said heterologous DNA fragment regulating the expression of at least one of said coding sequences in said target cell.

8. An isolated host cell infected with a virion according to claim 2.

9. An isolated non-human host cell infected with a virion according to claim 2.

10. A recombinant retroviral vector comprising,
 (a) a 5' long terminal repeat region comprising the structure U3-R-U5;
 (b) one or more coding sequences, said sequences being inserted into the body of the vector outside of the 5' and a 3' long terminal repeat regions, wherein at least one sequence encodes for at least one therapeutic antimicrobial peptide, wherein the antimicrobial peptide is selected from the group consisting of: cecropin, SB-37, Shiva-1, a preform thereof, a preproform thereof, a biologically active analogue thereof having antimicrobial activity, and a combination thereof; and
 (c) a 3' long terminal repeat region comprising a completely or partially deleted U3 region wherein said deleted U3 region is replaced by a polylinker sequence which comprises at least one unique restriction site and at least one insertion of a heterologous DNA fragments wherein the heterologous DNA fragment regulates the expression of at least one of the coding sequences of said vector, and comprises one or more elements selected from the group consisting of: regulatory elements and promoters, wherein after infection of a target cell, the U3 region of said 5' long terminal repeat region is replaced by said polylinker sequence, resulting in at least one of said coding sequences becoming operatively linked to said heterologous DNA fragment and said heterologous DNA fragment regulating the expression of at least one of said coding sequences in said target cell.

11. A recombinant retroviral vector system comprising:
 (a) a recombinant vector comprising,
  (i) a 5' long terminal repeat region comprising the structure U3-R-U5;
  (ii) one or more coding sequences, said sequences being inserted into the body of the vector outside of the 5' and a 3' long terminal repeat regions, wherein at least one sequence encodes for at least one therapeutic antimicrobial peptide, wherein the antimicrobial peptide is selected from the group consisting of: cecropin, a preform thereof, a preproform thereof, a biologically active analogue thereof having antimicrobial activity, and a combination thereof; and
  (iii) a 3' long terminal repeat region comprising a completely or partially deleted U3 region wherein said deleted U3 region is replaced by a polylinker sequence which comprises at least one unique restriction site and at least one insertion of a heterologous DNA fragments, wherein the heterologous DNA fragment regulates the expression of at least one of the coding sequences of said vector, and comprises one or more elements selected from the group consisting of: regulatory elements and promoters, wherein after infection of a target cell, the U3 region of said 5' long terminal repeat region is replaced by said polylinker sequence, resulting in at least one of said coding sequences becoming operatively linked to said heterologous DNA fragment and said heterologous DNA fragment regulating the expression of at least one of said coding sequences in said target cell, (b) a packaging cell line harboring at least one retroviral construct coding for proteins required for said recombinant vector to be packaged.

12. A retroviral particle produced by the recombinant retroviral vector system according to claim 11.

13. A retroviral provirus produced by infection of target cells with a recombinant retroviral particle according to claim 12 whereby the U3 region duplicated during the process of reverse transcription in the infected target cell and appears in the 5' long terminal repeat and the 3' long terminal repeat of the resulting provirus, and the U5 of the 5' long terminal repeat duplicated during the process of reverse transcription in the infected target cell and appears in the 3' long terminal repeat and in the 5' long terminal repeat of the resulting provirus.

14. The retroviral provirus of claim 13 wherein said polylinker comprises heterologous DNA.

15. A method for introducing nucleotide sequences into an isolated cell population comprising infecting the cell population with the retroviral particle according to claim 12.

16. A mRNA of a retroviral provirus produced by infection of target cells with a recombinant retroviral particle from a recombinant retroviral vector system comprising:
 (a) a recombinant vector comprising,
  (i) a 5' long terminal repeat region comprising the structure U3-R-U5;
  (ii) one or more coding sequences, said sequences being inserted into the body of the vector outside of the 5' and a 3' long terminal repeat regions, wherein at least one sequence encodes for at least one therapeutic antimicrobial peptide, wherein the antimicrobial peptide is selected from the group consisting of: cecropin, a preform thereof, a preproform thereof, a biologically active analogue thereof having antimicrobial activity, and a combination thereof; and
  (iii) a 3' long terminal repeat region comprising a completely or partially deleted U3 region wherein said deleted U3 region is replaced by a polylinker sequence which comprises at least one unique restriction site and at least one insertion of a heterologous DNA fragment, wherein the heterologous DNA fragment regulates the expression of at least one of the coding sequences of said vector, and comprises one or more elements selected from the group consisting of: regulatory elements and promoters, wherein after infection of a target cell, the U3 region of said 5' long terminal repeat region is replaced by said polylinker sequence, resulting in at least one of said coding sequences becoming operatively linked to said heterologous DNA fragment and said heterologous DNA fragment regulating the expression of at least one of said coding sequences in said target cell; and (b) a packaging cell line harboring at least one retroviral construct coding for proteins required for said recombinant vector to be packaged.

17. A RNA produced by a vector which wherein said vector comprises,
   (a) a 5' long terminal repeat region comprising the structure U3-R-U5;
   (b) one or more coding sequences, said sequences being inserted into the body of the vector outside of the 5' and a 3' long terminal repeat regions, wherein at least one sequence encodes for at least one therapeutic antimicrobial peptide, wherein the antimicrobial peptide is selected from the group consisting of: cecropin, a preform thereof, a preproform thereof, a biologically active analogue thereof having antimicrobial activity, and a combination thereof; and
   (c) a 3' long terminal repeat region comprising a completely or partially deleted U3 region wherein said deleted U3 region is replaced by a polylinker sequence which comprises at least one unique restriction site and at least one insertion of a heterologous DNA fragment, wherein the heterologous DNA fragment regulates the expression of at least one of the coding sequences of said vector, and comprises one or more elements selected from the group consisting of: regulatory elements and promoters,
   wherein after infection of a target cell, the U3 region of said 5' long terminal repeat region is replaced by said polylinker sequence, resulting in at least one of said coding sequences becoming operatively linked to said heterologous DNA fragment and said heterologous DNA fragment regulating the expression of at least one of said coding sequences in said target cell.

18. An isolated host cell infected with a virion according to claim 12.

19. An isolated non-human host cell infected with a virion according to claim 12.

20. A recombinant retroviral vector comprising,
   (a) a 5' long terminal repeat region comprising the structure U3-R-U5;
   (b) one or more coding sequences, said sequences being inserted into the body of the vector outside of the 5' and a 3' long terminal repeat regions, wherein at least one sequence encodes for at least one therapeutic antimicrobial peptide, wherein the antimicrobial peptide is selected from the group consisting of: melittin, cecropin, magainin, a preform thereof, a preproform thereof, a biologically active analogue thereof having antimicrobial activity, and a combination thereof; and
   (c) a 3' long terminal repeat region comprising a completely or partially deleted U3 region wherein said deleted U3 region is replaced by a polylinker sequence which comprises at least one unique restriction site and at least one insertion of a heterologous DNA fragment wherein the heterologous DNA fragment regulates the expression of at least one of the coding sequences of said vector, and comprises one or more elements selected from the group consisting of: regulatory elements and promoters,
   wherein after infection of a target cell, the U3 region of said 5' long terminal repeat region is replaced by said polylinker sequence, resulting in at least one of said coding sequences becoming operatively linked to said heterologous DNA fragment and said heterologous DNA fragment regulating the expression of at least one of said coding sequences in said target cell.

\* \* \* \* \*

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
        (A) LENGTH: 26 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:1:

Gly Ile Gly Ala Val Leu Lys Val Leu Thr Thr Gly Leu Pro Ala Leu
1               5                   10                  15

Ile Ser Trp Ile Lys Arg Lys Arg Gln Gln
                20                  25

(2) INFORMATION FOR SEQ ID NO:2:

(i) SEQUENCE CHARACTERISTICS:
        (A) LENGTH: 26 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:2:

Gly Ile Gly Ala Val Leu Lys Val Leu Thr Thr Gly Leu Pro Ala Leu
1               5                   10                  15

```
Ile Ser Trp Ile Gly Gly Gly Gly Gly Gly
         20                  25
```

(2) INFORMATION FOR SEQ ID NO:3:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:3:

TATGACGTCT CGTTAGAACG CGGCT     25

(2) INFORMATION FOR SEQ ID NO:4:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:4:

GGCAGATCTT AAATGTATCA TGCAAT     26

(2) INFORMATION FOR SEQ ID NO:5:

(i) SEQUENCE CHARACTERISTICS:
        (A) LENGTH: 6 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:5:

GACGTC     6

(2) INFORMATION FOR SEQ ID NO:6:

(i) SEQUENCE CHARACTERISTICS:
        (A) LENGTH: 6 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:6:

AGATCT     6

(2) INFORMATION FOR SEQ ID NO:7:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

```
         (xi) SEQUENCE DESCRIPTION: SEQ ID NO:7:

ATAGACGTCA AGGAAGGAAG CGATCGGA                                              28

(2) INFORMATION FOR SEQ ID NO:8:

(i) SEQUENCE CHARACTERISTICS:
          (A) LENGTH: 28 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "DNA"

(xi) SEQUENCE DESCRIPTION: SEQ ID NO:8:

TATGGATCCA ACCCTGTTGC CTCTTACG                                              28

(2) INFORMATION FOR SEQ ID NO:9:

(i) SEQUENCE CHARACTERISTICS:
          (A) LENGTH: 35 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "DNA"

(xi) SEQUENCE DESCRIPTION: SEQ ID NO:9:

TCTTACATCT ATGCGGGAAT TGGAGCAGTT CTGAA                                      35

(2) INFORMATION FOR SEQ ID NO:10:

(i) SEQUENCE CHARACTERISTICS:
          (A) LENGTH: 35 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "DNA"

(xi) SEQUENCE DESCRIPTION: SEQ ID NO:10:

AACTGCTCCA ATTCCCGCAT AGATGTAAGA AATGT                                      35

(2) INFORMATION FOR SEQ ID NO:11:

(i) SEQUENCE CHARACTERISTICS:
          (A) LENGTH: 6 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "DNA"

(xi) SEQUENCE DESCRIPTION: SEQ ID NO:11:

GACGTC                                                                       6

(2) INFORMATION FOR SEQ ID NO:12:

(i) SEQUENCE CHARACTERISTICS:
          (A) LENGTH: 6 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "DNA"
```

(xi) SEQUENCE DESCRIPTION: SEQ ID NO:12:

GGATCC                                                                                                              6